United States Patent
Prakash et al.

(10) Patent No.: US 10,302,924 B2
(45) Date of Patent: May 28, 2019

(54) OPTICAL MICROSCOPE

(71) Applicant: The Board of Trustees of the Leland Stanford Junior University, Stanford, CA (US)

(72) Inventors: Manu Prakash, San Francisco, CA (US); James Stanley Cybulski, Palo Alto, CA (US); James C. Clements, Everett, WA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/639,856

(22) Filed: Jun. 30, 2017

(65) Prior Publication Data

US 2018/0003937 A1 Jan. 4, 2018

Related U.S. Application Data

(63) Continuation of application No. 14/376,010, filed as application No. PCT/US2013/025612 on Feb. 11, 2013, now Pat. No. 9,696,535.

(60) Provisional application No. 61/597,682, filed on Feb. 10, 2012.

(51) Int. Cl.
*G01N 21/01* (2006.01)
*G02B 21/26* (2006.01)
*G02B 21/00* (2006.01)
*G02B 21/06* (2006.01)

(52) U.S. Cl.
CPC ......... *G02B 21/0076* (2013.01); *G01N 21/01* (2013.01); *G02B 21/0008* (2013.01); *G02B 21/06* (2013.01); *G02B 21/26* (2013.01)

(58) Field of Classification Search
None
See application file for complete search history.

(56) References Cited

U.S. PATENT DOCUMENTS

| | | | |
|---|---|---|---|
| 2,789,460 A | 4/1957 | Kaufman | |
| 2,986,830 A | 6/1961 | Underberg et al. | |
| 3,562,939 A | 2/1971 | Jacobs et al. | |

(Continued)

FOREIGN PATENT DOCUMENTS

| DE | 2644949 A1 | 4/1977 |
|---|---|---|
| DE | 19531819 A1 | 2/1997 |

(Continued)

OTHER PUBLICATIONS

Lorusso et al.; Experimental resolution measurement in critical dimension scanning electron microscope metrology; Scanning; 25(4); pp. 175-180; Dec. 6, 2003 (Abstract Only).

*Primary Examiner* — Derek S. Chapel
(74) *Attorney, Agent, or Firm* — Shay Glenn LLP

(57) ABSTRACT

An optical device, such as a microscope, is disclosed that can be assembled from flat materials. The optical device can be assembled via a series of folds of a flat material. The optical microscope can include a stage for supporting a sample, an optic stage, and a light source. The optic stage can include one or more lenses. The optical microscope can be capable of obtaining simultaneous images from different forms of microscopy. The optical microscope may have bright field and filter field viewing capabilities wherein a user shifts from bright field to filter field by lateral movement of the stage containing a lens and a light source that cooperate to provide either the bright field or the filter field.

24 Claims, 21 Drawing Sheets

(56) References Cited

U.S. PATENT DOCUMENTS

| | | |
|---|---|---|
| 3,734,596 A | 5/1973 | Nerlich |
| 3,756,699 A | 9/1973 | Martin |
| 3,900,252 A | 8/1975 | Di Salvo et al. |
| 4,095,874 A | 6/1978 | Wallace |
| 4,357,073 A | 11/1982 | Carver |
| 4,435,912 A | 3/1984 | Adrian et al. |
| 4,568,148 A | 2/1986 | Onanian |
| 4,729,635 A | 3/1988 | Saferstein et al. |
| 4,737,016 A | 4/1988 | Russell et al. |
| 4,945,220 A | 7/1990 | Mallory et al. |
| 5,062,697 A | 11/1991 | Mitchell |
| 5,198,927 A | 3/1993 | Rathbone et al. |
| 5,969,852 A | 10/1999 | Kung |
| 6,614,604 B1 | 9/2003 | Budde |
| 6,738,191 B1 | 5/2004 | Onanian |
| 6,847,480 B2 | 1/2005 | Steenblik et al. |
| 8,111,464 B2 | 2/2012 | Lee et al. |
| 9,696,535 B2 | 7/2017 | Prakash et al. |
| 2002/0048729 A1 | 4/2002 | Nishikawa et al. |
| 2002/0173045 A1 | 11/2002 | Schwartz |
| 2003/0095340 A1 | 5/2003 | Atwater et al. |
| 2004/0095641 A1 | 5/2004 | Russum et al. |
| 2004/0142386 A1 | 7/2004 | Rigler et al. |
| 2006/0028717 A1 | 2/2006 | Dunn |
| 2006/0254316 A1 | 11/2006 | Leu |
| 2008/0144192 A1 | 6/2008 | Choi et al. |
| 2008/0213495 A1 | 9/2008 | Miyauchi et al. |
| 2010/0073766 A1 | 3/2010 | Angros |
| 2010/0091364 A1 | 4/2010 | Wozniak |
| 2010/0259805 A1 | 10/2010 | Osipchuk |
| 2010/0284066 A1 | 11/2010 | Dunning et al. |
| 2011/0043796 A1 | 2/2011 | Markwort et al. |
| 2016/0025957 A1 | 1/2016 | Prakash et al. |

FOREIGN PATENT DOCUMENTS

| | | |
|---|---|---|
| GB | 2210177 A | 6/1989 |
| JP | 2003294419 A | 10/2003 |
| KR | 1020090059419 A | 6/2009 |
| WO | WO 00/20898 A2 | 4/2000 |

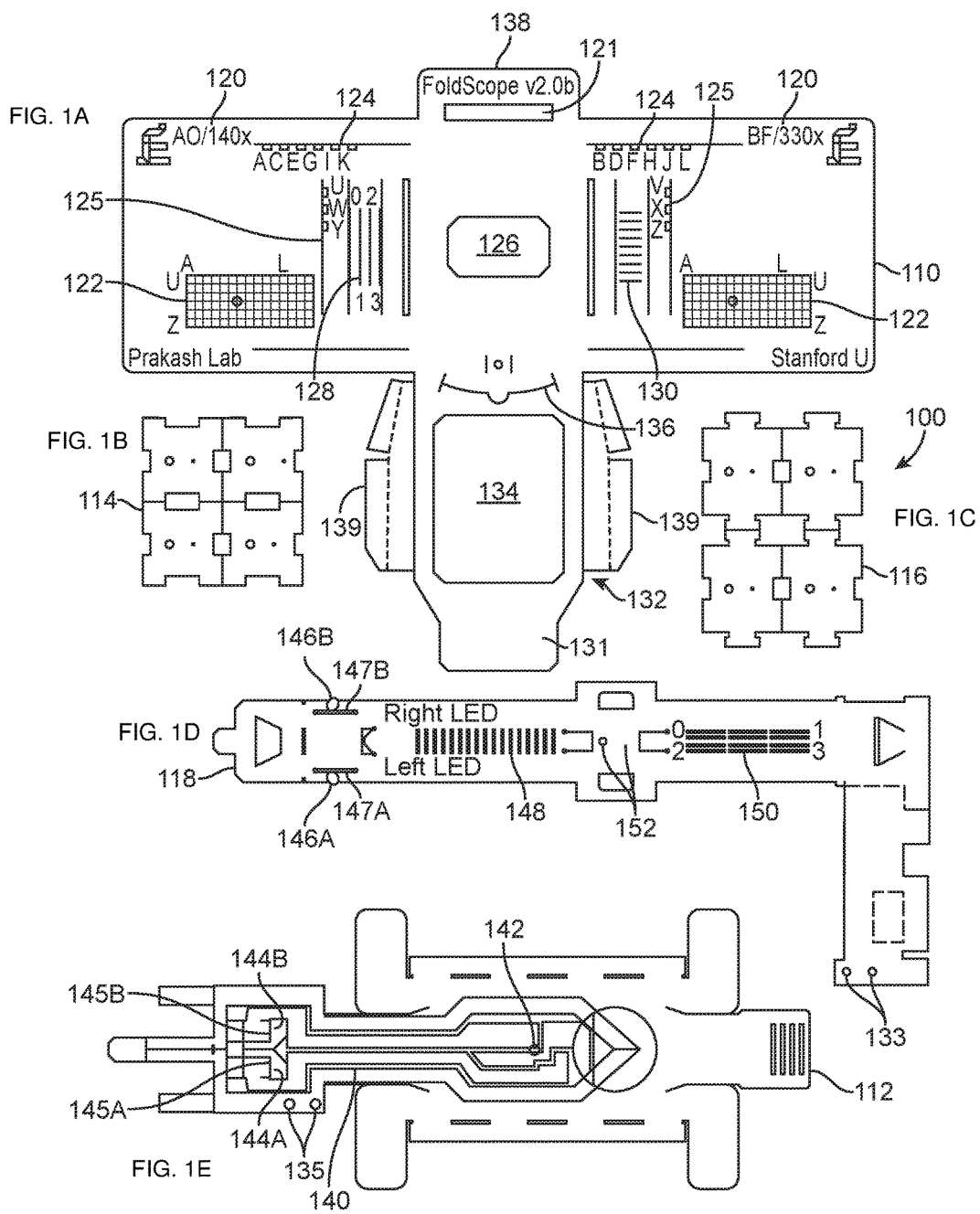

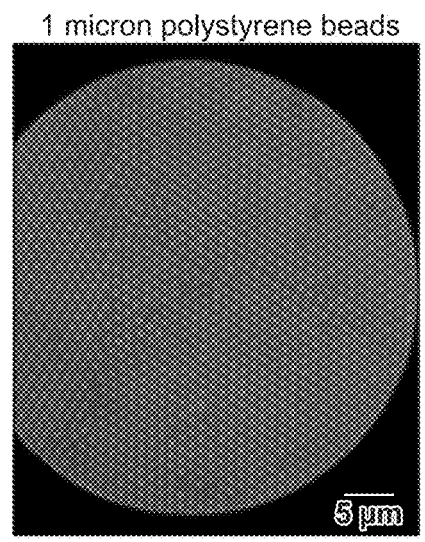
FIG. 18
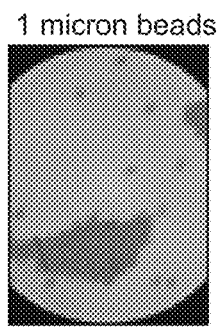
FIG. 19A
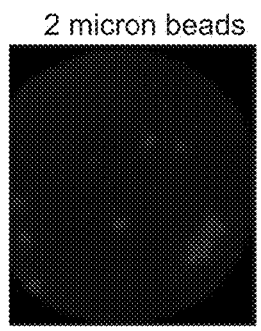
FIG. 19B
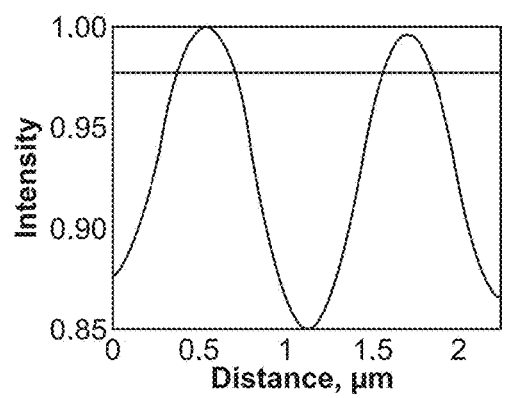
FIG. 19C
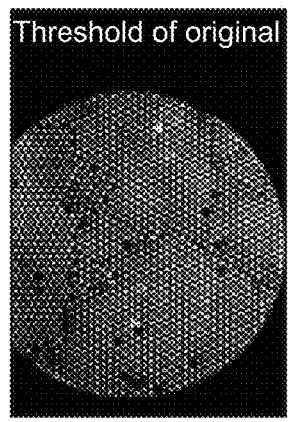 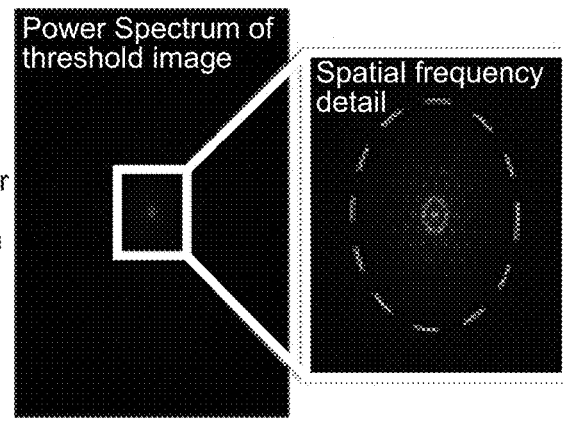
FIG. 19D Human Chromosomes DNA/RNA Stain Spinal Cord Skeletal Muscle

OPTICAL MICROSCOPE

CROSS REFERENCE TO RELATED APPLICATIONS

This application is a continuation of U.S. application Ser. No. 14/376,010, filed Jul. 31, 2014, which is a national stage filing under 35 U.S.C. § 371 of PCT/US2013/025612, filed Feb. 11, 2013, which claims the benefit under 35 U.S.C. 119 of U.S. Patent Application No. 61/597,682, filed Feb. 10, 2012, each of which is herein incorporated by reference in its entirety.

STATEMENT REGARDING FEDERALLY SPONSORED RESEARCH OR DEVELOPMENT

This invention was made with Government support under contracts RR025742 and TW008781 awarded by the National Institutes of Health. The Government has certain rights in this invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to diagnostic optical devices, such as microscopes.

BACKGROUND

An optical instrument is an instrument used to move light along a specified path or paths. Microscopes are common, general-purpose optical instruments. Other optical instruments include interferometers and spectrophotometers.

Microscopes are generally used to view objects that are too small to be seen by the unaided eye. Optical microscopes use visible light and a system of lenses to magnify images of small objects. Optical microscopes are used in observing small structures, determining pathology and diagnosing disease.

There are two basic configurations of the conventional optical microscope, the simple (one lens) and compound (many lenses). There are also several different types of microscopy including brightfield, darkfield, fluorescence, and other forms. Each of these forms of microscopy are performed individually and one at a time. High magnification optical microscopes are often heavy and take up much volume.

There is a need for improved optical instruments to better diagnose pathologies and disease.

SUMMARY OF THE DISCLOSURE

In some embodiments an optical device is provided. The optical devices can include a first stage for supporting a sample and a second stage engaged with the first stage and movable relative to the first stage, the second stage including an optic, the optic having a distance of less than about 3 mm from the sample to the opposite side of the optic. In some embodiments the optical device is an optical microscope. In some embodiments the optical device is an interferometer or spectrophotometers. In some embodiments the second stage can be movable laterally relative to the first stage such that the optic can be positioned over a desired location on the sample.

In some embodiments the first stage is configured to receive a substrate containing the sample. In some embodiments the first stage includes a slot shaped to receive the substrate. In some embodiments the substrate is a glass slide. In some embodiments the glass slide includes a portion treated with a reagent to interact with the sample. In some embodiments the sample is supported directly on the first stage. In some embodiments the first stage includes a sample area comprising a reagent to react with the sample.

In some embodiments the optical device includes an illumination stage comprising a light source. The illumination stage can be engaged with the first stage and second stage with the illumination stage movable with the second stage. The light source can be positioned adjacent to the first stage to facilitate viewing the sample using the optic.

In some embodiments the light source is on one side of the first stage and the optic is spaced apart from the opposite side of the first stage a distance between the light source and the side of the optic farthest from the first stage is less than about 5 mm. In some embodiments the light source is on one side of the first stage and the optic is spaced apart from the opposite side of the first stage a distance between the light source and the side of the optic farthest from the first stage is from about 1 mm to about 20 mm.

In some embodiments the light source includes one or more light-emitting diodes (LEDs). In some embodiments the LED is white to provide a full-spectrum color image of the sample in bright-field. In some embodiments the LED is blue to provide light of an appropriate wavelength for fluorescence imaging. In some embodiments the LED has an output power suitable to project an image of the sample. In some embodiments the LED has a power suitable to illuminate the sample so that a user's eye may perceive the image of the sample. In some embodiments the LEDs have power suitable so that a user may perceive multiple simultaneous images of the sample.

In some embodiments the optical device includes an illumination stage with an aperture. In some embodiments the illumination stage includes an aperture having a diameter of about ¼ to about ⅔ of the diameter of the substantially spherical lens. In some embodiments the optical microscope includes an illumination stage with an element for modifying the profile of the light from the LED, such as a condenser, diffuser, light shaping diffuser, polycarbonate light shaping filter, etc. In some embodiments, optical microscope has an illumination stage that provides Kohler illumination.

In some embodiments the optical device is manufactured from a flat material that includes the first stage and second stage. In some embodiments a single material piece provides the first stage and second stage. In some embodiments the flat material comprises one or more of paper, polymer, and metal.

In some embodiments a power source is provided with the optical microscope. The power source can engage with the illumination stage and is configured to provide power to the light source.

In some embodiments the microscope optic comprises a substantially spherical ball lens. In some embodiments the substantially spherical ball lens has a diameter of less than about 2,500 μm. In some embodiments the spherical ball lens has a diameter of about 1,000 μm to about 2,500 μm. In some embodiments the spherical ball lens has a diameter of about 300 µm to about 1,000 µm. In some embodiments the spherical ball lens has a diameter of about 100 µm to about 300 µm. In some embodiments the spherical lens has a diameter of about 200 µm to about 1,000 µm.

In some embodiments the spherical lens has an effective aperture of less than the diameter of the spherical lens. In some embodiments the aperture is about ¼ to about ⅔ of the diameter of the spherical lens. In some embodiments the spherical ball lens has an aperture diameter of about ¼ to ⅓ the lens diameter. In some embodiments the spherical lens has an aperture diameter of about ⅓ to ½ the lens diameter. In some embodiments the spherical lens has an aperture diameter of about ½ to ⅔ the lens diameter. In some embodiments half-ball spherical lenses can be used. In some embodiments a Wallston doublet lens is utilized. The Wallston doublet lens can be composed of multiple half ball lenses. In some embodiments a Gradient Index lens is used.

In some embodiments the optical microscope is manufactured from a flat material that includes the first stage, second stage, and illumination stage. In some embodiments, the optical microscope is manufactured in a single instance. In some embodiments, a series of folds produce the final configuration of the microscope. The optical microscope can have an optical alignment of the illumination stage, first stage, and second stage achieved passively by separating and folding the flat material. The optical alignment can have an accuracy of about 10 microns or less.

In some embodiments, the folding accuracy is accomplished by geometrical features cut in flat material that act as kinematic couplings thus providing a self-alignment. In some embodiments, self-alignment is further improved by providing structural closed loops in folding steps.

In some embodiments, the optical microscope can have an integrated microfluidic channel for bringing samples directly to the microscope lens.

In some embodiments, the optical microscope can be incinerated after one use safely and thus can be used with infected samples.

In some embodiments, the entire microscope is disposable after single or multiple uses.

In some embodiment, a waveguide is utilized to channel light from the light source to other optical components.

In some embodiments the second stage of the optical microscope includes an opening with the lens in the opening.

In some embodiments the microscope has a magnification of about 100× to 200×. In some embodiments the microscope has a magnification of about 200× to 500×. In some embodiments the microscope has a magnification of about 500× to 1,500×. In some embodiments the microscope has a magnification of about 1,500× to 2,500×. In some embodiments the microscope has a magnification of greater than about 300×. In some embodiments the microscope has a magnification of greater than about 140×. In some embodiments the microscope has a magnification of greater than about 1000×.

In some embodiments the microscope has a resolution of about 2.0 to 3.0 microns. In some embodiments the microscope has a resolution of about 1.5 to 2.0 microns. In some embodiments the microscope has a resolution of about 1.0 to 1.5 microns. In some embodiments the microscope has a resolution of less than about 1.0 microns. In some embodiments the microscope has a resolution of about 0.88 to 1.0 microns. In some embodiments the microscope has a resolution of about 0.6 to 0.88 microns. In some embodiments the microscope has a resolution of 0.2 to 0.5 microns.

In some embodiments the first stage for supporting sample comprises a diagnostic coating for providing a visual indication to a user through the optical microscope of a presence of a diagnostic target. In some embodiments the visual indication is viewed using the optic. In some embodiments the diagnostic target is a disease, parasite, bacteria, or disorder detectable in a bodily fluid.

In some embodiments the optic includes an array of lenses. In some embodiments the array of lenses simultaneously shows one or more bright field images and one or more fluorescence images. In some embodiments the array of lenses includes four or more lenses.

In some embodiments the optical microscope is a bright field microscope. In some embodiments a colored LED and/or light filter is used and the optical microscope is a fluorescence microscope, polarization microscope, phase contrast microscope, etc.

In some embodiments the optical microscope has bright field and filter field viewing capabilities wherein a user shifts from bright field to filter field by lateral movement of the second stage and the light source that cooperate to provide either the bright field or the filter field.

In some embodiments the optical microscope includes a marking aperture on the second stage configured to allow a user to identify and indicate a target location on the sample by marking the first stage through the marking aperture on the second stage such that a second user can align the optical microscope to view the target location. In some embodiments, an optimal aperture is utilized for the series of lenses used in the microscope in order to minimize the imaging artifacts.

In some embodiments, the optical microscope includes a tool for cleaning debris from the lens. The cleaning tool can be comprised of a glass slide with a piece of lens paper attached to the surface.

Methods for using optical microscopes are disclosed herein. The methods can include engaging a first portion of an optical microscope configured to support a sample with a second portion of an optical microscope having a lens; placing a sample on the first portion of the optical microscope; adjusting the lens by moving the second portion of the optical microscope having the lens relative to the first portion of the optical microscope to focus on the sample; and viewing the sample. In some embodiments during the adjusting step the optical microscope has an optical path distance of less than about 3 mm from the sample to the opposite side of the optic.

In some embodiments before the adjusting step or the viewing step is a step of placing a portion of the microscope against a user's eyebrow. In some embodiments viewing the sample comprises projecting an image of a portion of the sample. In some embodiments adjusting the lens includes moving the second portion relative to the first portion in an out-of-plane direction from a distance of about 5 µm to about 625 µm. In some embodiments viewing the sample comprises buckling the second portion to adjust the distance between the lens on the second portion and the sample.

In some embodiments before viewing the sample is reacted with a reagent. In some embodiments viewing the sample comprises testing the sample for a disease.

In some embodiments the methods include, before engaging, removing the first portion and the second portion form a single piece of a flat material. In some embodiments engaging includes assembling the optical microscope from a flat material. In some embodiments assembly of the optical microscope involves origami or folding of a flat sheet of material In some embodiments, the sample is reacted to a reagent already deposited in the sample holding stage via a microfluidic network embedded in the sample holding stage. In some embodiments, the reagent is dried for preservation. In some embodiments, the reagent is wet.

In some embodiments an optical microscope is provided including a stage; a lens; and a light source. The optical microscope having bright field and filter field viewing capabilities wherein a user shifts from bright field to filter field by lateral movement of the stage containing a lens and a light source that cooperate to provide either the bright field or the filter field. In some embodiments the lateral movement of the stage to move between bright field and filter field is less than 10 mm. In some embodiments the lens can be engaged a strip having tabs with the strip configured to allow a user to slide the tabs to buckle the strip or adjust the focal length. In some embodiments sliding the tabs attached to the lens focuses the image or moves the lens closer to the user's eye.

In some embodiments an optical microscope is provided, including a stage; a lens; a light source; and an enclosure having an enclosed volume of 70 cubic centimeters or less which contains the stage, lens and light source. In some embodiments the enclosed volume is 175 millimeters×70 millimeters×5.7 millimeters. In some embodiments the optical microscope further comprises a container configured to store more than twenty optical microscopes within a volume of 1,400 cubic centimeters or less. In some embodiments the container configured to store a range of 20-50 optical microscopes.

In some embodiments, the lens can be cleaned by inserting a slide with lens paper attached to the surface and panning the second stage in circles over the lens paper so that the lens paper brushes off contaminants from the surface of the lens.

In some embodiments, optical instruments including interferometers and spectrophotometers are constructed using the principles disclosed herein to achieve a desired beam path.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1E illustrate the components for assembly into an exemplary optical microscope.

FIG. 18 illustrates an image of 1 µm polystyrene beads using a 300 µm ball lens and an aperture size of about 150 µm.

FIG. 19A illustrates a bright field image of 1 µm polystyrene beads. FIG. 19B illustrates a fluorescent image of 2 µm polystyrene beads. FIG. 19C illustrates a plot of intensity versus distance. FIG. 19D illustrates an image of polystyrene beads along with a 2D-Fourier transform showing the power spectrum of the threshold image and spatial frequency detail.

FIG. 25B shows the undamaged optical microscope after being stepped on.

DETAILED DESCRIPTION

Figure 2A:
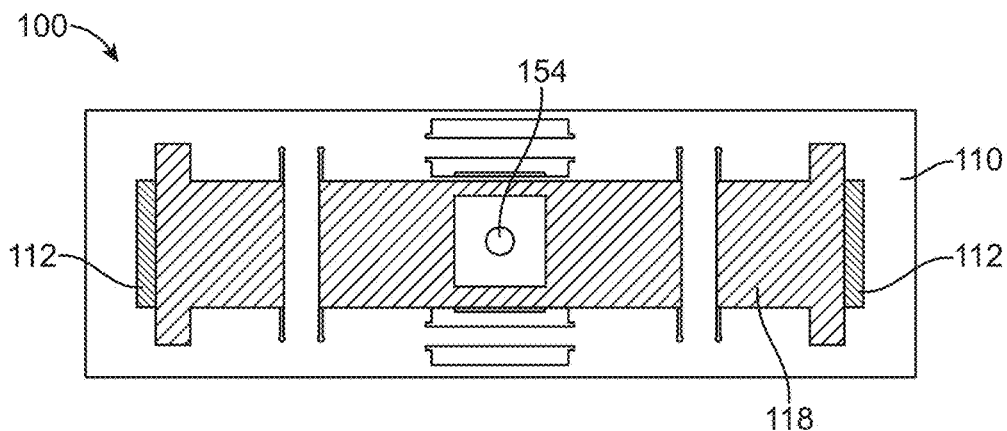
FIG. 2A illustrates a top view of an exemplary optical microscope.

Optical devices and methods for using optical devices, such as microscopes are disclosed herein. The optical devices disclosed herein can be assembled from a flat material. The flat material can include one or more lenses, a sample support, illumination sources, and control electronics. The optical devices can be an optical microscope, interferometer, and spectrophotometers. The optical devices can be designed and assembled based on Origami principles and optical design principles. For example, the individual components of the optical devices can be designed based on Origami principles. The components can be designed to facilitate assembly and alignment of the optical device.

A microscope can be a critical tool for disease diagnostics, especially in resource poor settings around the world. Conventional microscopes were designed as general-purpose research tools. Conventional microscopes are costly and not designed with portability in mind. Traditional microscopes are also prone to failure in harsh field conditions since they are complex three-dimensional objects that are costly, bulky and require regular maintenance for optimal performance. In addition, traditional optical instruments require significant alignment post assembly.

The optical devices disclosed herein can be assembled in the field from a flat material and assembled to achieve the optical alignment. The achievement of the optical alignment through folding and engagement of the components can be referred to as passive alignment. Passive alignment can be achieved through kinematic constraints and structural loops. The optical devices and individual components of the optical can be shaped to facilitate passive alignment. Passive alignment great reduces the costs associated with the optical devices and allows for the optical devices to be assembled in environments without the resources for assembling and aligning a conventional optical device, such as an optical microscope.

The components of the optical microscope can be formed, printed, or applied on the flat flexible substrate. Examples of flat materials include paper, thin metal, polymers, paper coated with polymers, polyamide, Flex PCBs, etc. The flat material can be flexible and is not limited to a planar configuration.

In some embodiments other optical instruments can be constructed using the folding principles disclosed herein to achieve a desired optical or beam path in 3 dimensions. Examples of optical instruments include interferometers, spectrophotometers, and other optical instruments.

The optical devices can be assembled from the flat material using a series of cutting and folding steps. The optical microscopes disclosed herein can be designed to self-align due to kinematic constraints present in how the optical microscope is assembled from the flat materials. The optical microscope can be designed with folds and mating stages that self align the one or more lenses with the sample support and any illumination sources when assembled. Mechanical components such as a panning and focus stage can be implemented as flexure mechanisms manufactured by folding paper. The panning stage can allow for movement in the X-Y direction to position the optic over any portion of a sample. For a 2 cm by 2 cm sample the panning stage can include a travel distance of 2 cm by 2 cm.

The optical device can be a multi-modal microscope implementing one or more of bright field, multi-fluorescence, polarization, phase contrast, and projection microscopy. The optical microscope can include a filter for fluorescence and polarization modalities. For projection microscopy the optical microscope includes a light source with a power suitable to project an image. For example, the light source may consume 800 mA of electrical current at 3.7V.

The sample can be viewed through the optic. In some embodiments the user can position the optical microscope close to their face, such that the optic is located about 5 cm or less from the user's retina. In some embodiments the optical microscope can project an image. For example, the image can be projected on a flat surface such as a screen. Alternatively, the optical microscope can use a screen designed to conform to the shape of the Petzval surface of the lens to eliminate field curvature in the projected image.

The optical microscope can include an array of lenses. The lenses can have different sizes and magnifications. The lenses in the array can also be used to provide images of different modalities simultaneously, e.g. two different fluorescence images or a bright field image and a fluorescence image. The array of lenses can be provided in a side by side arrangement. The multiple lenses can be paired with one or more light sources. The array of lenses can be arranged in a grid, e.g. in a 3×3 grid arrangement.

The optical microscopes can have an optical path that is much shorter than conventional microscopes. For example, the optical path can include the distance between the light source and the opposing side of the lens. In some embodiments the distance between the light source and the opposing side of the optic or lens is from about 1 mm to about 20 mm. In some embodiments the optical path is less than about 5 mm. In some embodiments the optical path is less than about 3 mm. The short optical path allows for the microscope to be a much smaller vertical height, assuming a vertical optical path, in comparison to traditional optical microscopes. The shorter vertical height requires less structural support and less material, thereby decreasing manufacturing costs. In some embodiments the optical path between the sample and the opposing side of the optic is less than about 3 mm. In some embodiments the optical path between the sample and the opposing side of the optic is less than about 2 mm or less than about 1 mm. These short optical paths can allow for illuminating the sample with a much lower power light source or lower amount of light versus conventional microscopes.

Unlike a traditional microscope, the entire optics and illumination stage can be panned across the surface of the sample slide, which can be fixed in a single location. The optical microscopes disclosed herein can have a lens and light source that are movable relative to the sample or sample stage. An optic stage can include a support for the lens. The light source can be integrated with a separate stage, such as an illumination stage. The optic stage and illumination stage can be engaged such that they move together. The lens can move along above the sample along an x-axis and y-axis to observe different areas of the sample. In addition the vertical distance, e.g. along a z-axis, between the lens and sample can be adjusted.

The optical microscopes disclosed herein can be used for a variety of applications. The optical microscopes can be used for diagnostic applications such as testing for a disease, parasite, bacteria, or disorder that is detectable in a bodily fluid. Examples include diagnostic applications such as diagnosing diseases such as Malaria, Chagas, Giardiasis, Microfilariasis, Sickle-cell disease, and other diseases. Stains for common parasites and diseases can be used with the samples. The sample and stain can be observed with the optical microscope to determine the presence or absence of the diagnostic target. The optical microscopes can also be used for general purposes, including science education.

Figure 8A:
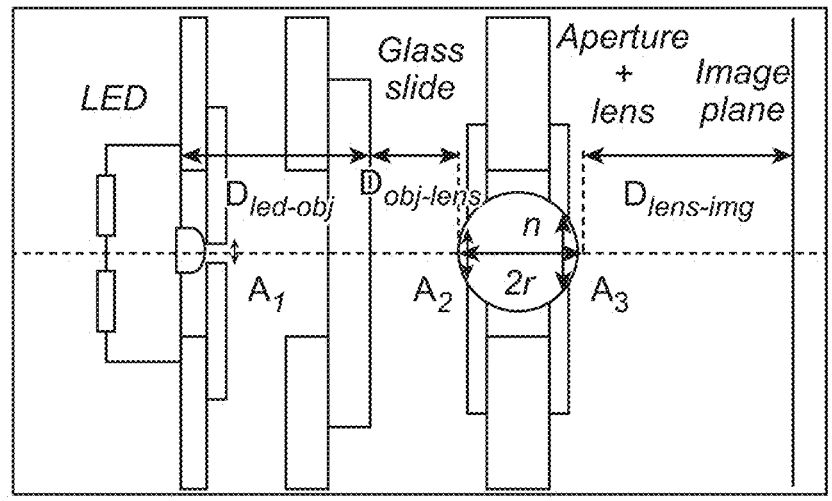
FIG. 8A illustrates an exemplary optical path of an optical microscope in accordance with an embodiment.

In some embodiments the lens is a substantially spherical lens, for example a ball lens. A ball lens advantageous for manufacturing because it can minimize part count and be assembled without concern for rotational alignment as shown in FIG. 8A. Ball lenses can be formed from molten glass or UV-curable epoxies. Suspension polymerization can also be used to produce spherical GRIN lenses with reduced spherical aberration. Other examples of ball lens materials include borosilicate, sapphire, BK-7, polymeric materials such as acrylic, etc.

Figure 9A:
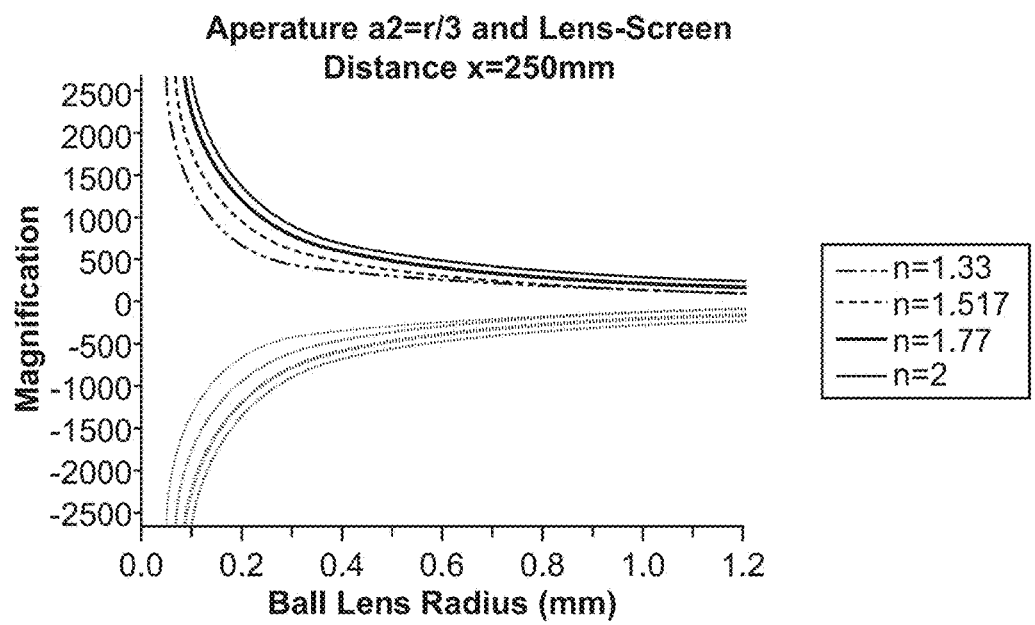
FIG. 9A illustrates the magnification obtained versus various lens radii for different refractive index values.

The ball lens can be sized based on the desired magnification of the optical microscope. As shown in FIG. 9A the magnification varies inversely with the ball lens radius. For a high magnification, e.g. above 500×, the ball lens can have a small radius, such as below 0.5 mm. The small lens size allows for a thinner optical microscope thickness and smaller form factor. In some embodiments the ball lens has a diameter of less than about 2,500 microns. In some embodiments the spherical ball lens has a diameter of about 1,000 μm to about 2,500 μm. In some embodiments the ball lens has a diameter of less than about 1,000 microns. In some embodiments the spherical ball lens has a diameter of about 300 μm to about 1,000 μm. In some embodiments the ball lens has a diameter of about 100 microns to about 1,000 microns. In some embodiments the ball lens has a diameter of about 100 microns to about 3,000 microns. In some embodiments the spherical ball lens has a diameter of about 100 μm to about 300 μm.

In some embodiments half-ball spherical lenses can be used. In some embodiments a Wallston doublet lens is utilized. The Wallston doublet lens can be composed of multiple half ball lenses. In some embodiments a Gradient Index lens is used.

In some embodiments the effective aperture of the substantially spherical lens in the optical microscope can be less than the full diameter of the spherical lens. For example, a portion of the spherical lens can be covered or removed to reduce the effective aperture of the spherical lens as discussed in detail below. In some embodiments the aperture is about ¼ to about ⅔ of the diameter of the spherical lens. In some embodiments the spherical ball lens has an aperture diameter of about ¼ to about ⅓ of the spherical lens diameter. In some embodiments the spherical lens has an aperture diameter of about ⅓ to about ½ of the spherical lens diameter. In some embodiments the spherical lens has an aperture diameter of about ½ to about ⅔ of the spherical lens diameter.

The components of the optical microscopes can be selected to achieve a desired magnification and resolution as discussed in detail below. In some embodiments the optical microscope has a magnification of about 100× to about 200×. In some embodiments the optical microscope has a magnification of greater than about 140×. In some embodiments the optical microscope has a magnification of about 200× to about 500×. In some embodiments the optical microscope has a magnification of greater than about 300×. In some embodiments the optical microscope has a magnification of greater than about 500×. In some embodiments the optical microscope has a magnification of about 500× to 1,500×. In some embodiments the optical microscope has a magnification of greater than about 1000×. In some embodiments the optical microscope has a magnification of greater than about 1500×. In some embodiments the optical microscope has a magnification of about 1,500× to 2,500×. In some embodiments the optical microscope has a magnification of greater than about 2000×. In some embodiments the optical microscope has a magnification of greater than about 2500×.

In some embodiments the microscope has a resolution of about 2.0 to about 3.0 microns. In some embodiments the microscope has a resolution of about 1.5 to about 2.0 microns. In some embodiments the microscope has a resolution of about 1.0 to about 1.5 microns. In some embodiments the microscope has a resolution of about 0.88 to about 1.0 microns. In some embodiments the microscope has a resolution of about 0.6 to about 0.88 microns. In some embodiments the microscope has a resolution of less than about 1.0 microns. In some embodiments the microscope has a resolution of 0.2 to 0.5 microns.

Examples of light sources include sun light, LED lights, a lamp, indoor lighting, incandescent lighting, fluorescent lighting, a flame, chemiluminescence source such as a glow stick, and other light sources.

In some embodiments the light source is an LED light. In some embodiments the LED is white. A white LED can provide a full-spectrum color image of the sample in brightfield. In some embodiments the LED is blue. A blue LED can provide light of an appropriate wavelength for fluorescence imaging. In some embodiments the LEDs have power suitable so that a user may perceive multiple simultaneous images of the sample. In some embodiments the LED has a luminous emittance of about 1-100 kLux or more, which is suitable to project an image of the sample. In some embodiments the LED has a power of about 10-1,000 Lux, which is suitable to illuminate the sample so that a user's eye may perceive the image of the sample.

In some embodiments the light source can be coupled to an illumination stage. In some embodiments the optical device or microscope includes an illumination stage with an element for modifying the profile of the light from the light source (e.g. LED), such as a condenser, diffuser, light shaping diffuser, polycarbonate light shaping filter, etc. The illumination stage can also include a condenser to focus the light from the light source. Filters can also be used with the illumination stage. Examples of filters include polarization filters, polymer color filters, diffusive filters, and fluorescence filters. In some embodiments, optical microscope has an illumination stage that provides Kohler illumination.

In some embodiments the illumination stage includes an aperture or hole for allowing light to pass through the illumination stage towards the sample. The illumination stage aperture can be sized based on the size and diameter of the lens. In some embodiments the aperture has a diameter of about ¼ to about ⅔ of the diameter of the lens A power source, such as a battery, can be used to provide power to the light source. The power source can be coupled to the illumination stage.

The sample can be provided to the optical microscope on a substrate. The substrate can include a coating or reagent. In some embodiments the substrate can be provided on the flat material having the optic stage, sample stage, and illumination stage. In some embodiments the sample is provided on a glass slide.

FIGS. 1A-1E illustrate the components for assembly into an exemplary optical microscope. The optical microscope 100 includes sample or specimen stage 110, an illumination stage 112, a spacer insert 114, a locking spacer insert 116, and an optics stage 118. In various embodiments, the optical microscope 100 may not include an illumination stage 112. In the embodiment without an illumination stage 112, the illumination source may be an external source, such as the sun, a lamp, a candle or some other source. Components 110-118 may be part of a single flat sheet of paper that may be used to implement the optical microscope. The specimen stage 110 may include microscope identifiers 120, grid 122, horizontal position indicators 124, vertical position indicators 125, specimen illumination window 126, vertical fine position indicator 128, horizontal fine position indicator 130, slide sleeve 132 and slide viewing window 134. In the illustrated embodiment, horizontal position indicators 124 are denoted by the letters A-L and vertical position indicators 125 are denoted by the letters U-Z. Each letter A-L and U-Z of the horizontal position indicators 124 and vertical position indicators 125, respectively, may advance in increments of 2 mm. Any increment may be implemented. The microscope identifiers 120 may give the specification information that may include the microscope modality and magnification.

Grid 122 may be used along with horizontal position indicators 124, vertical position indicators 125, vertical fine position indicator 128, and horizontal fine position indicator 130. Specimen illumination window 126 may be an aperture or hole that allows a user to view a sample. Slide sleeve 132 may be folded over specimen illumination window 126 of specimen stage 110. Slide sleeve 132 may include slide slot 136 and slide tab 131. Slide tab 131 may be inserted into tab slot 121 during assembly. The size of each of the slide sleeve 132, slide slot 136, slide tab 131, slide slot 136, slide guides 139 and tab slot 121 may control the force that holds the slide in place. In various embodiments, the size of each of the slide sleeve 132, slide slot 136, slide tab 131, slide slot 136, slide guides 139 and tab slot 121 is configured to allow the slide to be easily inserted and positioned. In various embodiments, the size of each of the slide sleeve 132, slide slot 136, slide tab 131, slide slot 136, slide guides 139 and tab slot 121 is configured to maintain an original position and resist movement after the sample slide is inserted. A slide containing a sample may be inserted through slide slot 136 into slide sleeve 132. Slide guides 139 along the edges of slide sleeve 132 may be folded over to help guide insertion of the slide. The sample slide (not shown) may be positioned over specimen illumination window 126. The edge of the sample slide is lined up so that it is adjacent to a longitudinal edge 138.

Specimen stage 110 includes a mechanism for reproducing microscope settings. The mechanism is implemented by grid 122, vertical fine position indicator 128, horizontal fine position indicator 130, horizontal position indicator 124, vertical position indicator 125 and slide sleeve 132.

The illumination stage 112 may include circuitry 140, light source 142, and contact pads 144A-B. Circuitry 140 may include copper tape, conductive paper, conductive ink, or any other flat conductive material. The circuitry 140 can control the power supply to light source 142. In various embodiments, the power supply includes a battery. Light source 142 may include one or more LED lights, a lamp, a chemiluminescence source such as a glow stick, or other source. Illumination can be enhanced via a condenser lens 157 (located between 156 and 158). Contact pads 144A-B may establish contact with contacts on the optics stage 118. Illumination stage 112 may be mounted to specimen stage 110. In various embodiments, the optics stage 118 and the illumination stage 112 remain aligned within 0.5 mm or better during panning and focusing. This may be accomplished by connecting tabs 145A-B in the illumination stage 112 into the slots 147A-B in the optics stage 118.

A light source using chemiluminescence uses a chemical reaction as the illumination or light source. Liquid light sources may flow into a tube or flat chamber and allow for a wide array of optical designs. The liquid light source may move translationally so that the user sees the entire sample. Usually, one only has 2 degrees of freedom; the present disclosure allows vision of everything on the slide. Additionally, the present disclosure may allow for a configuration of a tube within a tube. A liquid light source within inner tube may illuminate a sample located between the inner tube and the outer tube. This design requires "zero power" to remove the need for a power source such as a battery or button cells.

Spacer insert 114 and locking spacer insert 116 may be used to position the lens (not shown) and adjust the optics of the optical microscope 100. One or more spacer inserts 114, 116 may be attached to illumination stage 112. One or more spacer inserts 114 may be positioned first. The locking spacer insert 116 is positioned over the one or more spacer inserts 114 to lock or hold them in position.

Optics stage 118 may include contacts 146A-B, vertical slits 148, horizontal slits 150, and lens apertures 152. Optics stage 118 is mounted to illumination stage 112 and specimen stage 110. Contacts 146A-B are designed to align with contact pads 144A-B. By depressing contacts 146A or 146B, a circuit is closed with light source 142 and a power source causing light source 142 to illuminate.

Vertical slits 148 and horizontal slits 150 align with vertical fine position indicator 128 and horizontal fine position indicator 130, respectively. As the sample slide is moved to the left horizontally, the horizontal fine position indicators 130 advance in that direction as it goes from one line to the next. In various embodiments, each horizontal line of horizontal fine position indicator 130 may represent a specific increment such as 0.5 mm. If a user sees two solid lines at the same time, the position is in between increments such as 0.25 mm. Any increment may be implemented. A location may be determined by the horizontal position indicators 124 and the vertical position indicators 125. For example, as a user looks at the left side of the optical microscope 100, a mark (not shown) indicates the horizontal position is at A or B. The vertical position may be determined similarly using vertical position indicators 125, X, Y, and Z, and may have similar increments. Vertical fine position indicator 128 and horizontal fine position indicator 130 may compliment vertical position indicators 125 and horizontal position indicator 124 by providing more detailed alignment information.

The optical microscope 100 may be created using a flat manufacturing process. Components may be together on a flat sheet that can be cut out and folded into an optical device. A design of pre-cut sheets can be created, downloaded, printed and used. Several integrated microscopes can be contained in one such optical microscope, creating different optical microscopes based on how the paper/material is folded. The present microscope may be a single-use microscope and is suitable for the present technology because the overall manufacturing process is inexpensive enough to discard or incinerate after use.

Figure 2B:
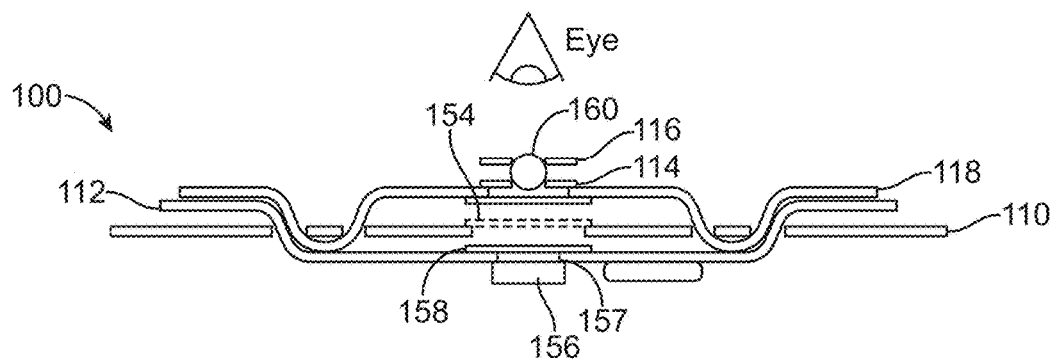
FIG. 2B illustrates a cross-sectional view of the optical microscope of FIG. 2A.

FIG. 2A illustrates a top view of an exemplary optical microscope. FIG. 2B illustrates a cross-sectional view of the optical microscope of FIG. 2A. The optical microscope 100 of FIGS. 2A-B include specimen stage 110, illumination stage 112, optics stage 118, and sample 154. Sample 154 may be viewed through slide viewing window 134 (See FIG. 1). Light source 156 may direct light through filter 158, condenser 157, sample 154, specimen illumination window 126 and is received by lens 160. Lens 160 may be positioned between spacer inserts 114 and locking spacer insert 116. In some embodiments, a second lens may be implemented between sample 154 and light source 156. In some embodiments an array of lenses are used. In some embodiments a condenser is used to shape the light and improve resolution.

Focusing the optical microscope 100 can be shown with reference to FIG. 2B. Focusing the lens 160 can be implemented by a flexure mechanism that uses a cantilever beam of paper being pinched at two points for a symmetric upward and downward motion of the embedded optics as shown in FIG. 2B. Tension or compression of the optics stage 118 causes a Z-axis scan via a flexure mechanism. The flexure mechanism can have a maximum travel distance of about 1 mm. The flexure mechanism can converts purely translational pinching movement along the X-axis to upward or downward motion along the Z-axis. The distance between the lens 160 and the sample 154 can be adjusted by pushing or pulling on the ends of the optics stage 118. Pushing the ends of the optics stage towards each other causes the lens 160 to raise thereby increasing the distance between the lens 160 and the sample 154. Pulling the ends of the optics stage 118 away from each other lowers the lens 160 thereby decreasing the distance between the lens 160 and the sample 154. The movement of the lens 160 towards and away from the sample 154 can be referred to as movement along the z-axis. In the case when there are two lenses (as shown in FIG. 5C), the lenses may be a certain distance apart. In various embodiments, the lenses may be about 6 mm apart. In other embodiments, the lenses may be about 5.5 mm apart. If a user finds something in left lens and wants to look at the same article/item with the right lens, the user may put a mark on grid 122. A marking instrument such as a pen or pencil may be inserted through marking apertures 133 in the optics stage 118 and marking apertures 135 in the illumination stage 112 to mark a position on grid 122. The user then moves the optics stage 118 so that it is lined up with the mark on grid 122. This may also allow a second user to find and view the same article/item using markings created by the first user. For example, a lab technician may be able to easily locate a particular pathology that has been indicated by markings on grid 122. The marking apertures can be used in any of the lens arrangements described herein. The marking apertures can have a precision of 0.5 mm or less.

The optical design may include focusing features, zoom features, panning features, and/or other features. Lens 160 may have a magnification of 140×, 340×, 680×, and 1140× corresponding to a borosilicate ball lenses with diameters of 2.4 mm, 1.0 mm, 0.5 mm, and 0.3 mm, respectively, as well as other magnifications. A variety of materials may be used for the lens. The lens may have a short path length due to the flat optical design that reduces signal-to-noise ratio for fluorescence. The path length may be symmetric or asymmetric. An asymmetric path length is created with a filter, a specimen, another filter, a ball lens on the top side, a light source and a light receiver. If a ball lens is placed on the bottom, the microscope becomes symmetric. The second lens may correct for the LED's divergence, making the light rays parallel rather than diverging, optimizing the LED. The LED may also act as a point source depending on the design.

Figure 3:
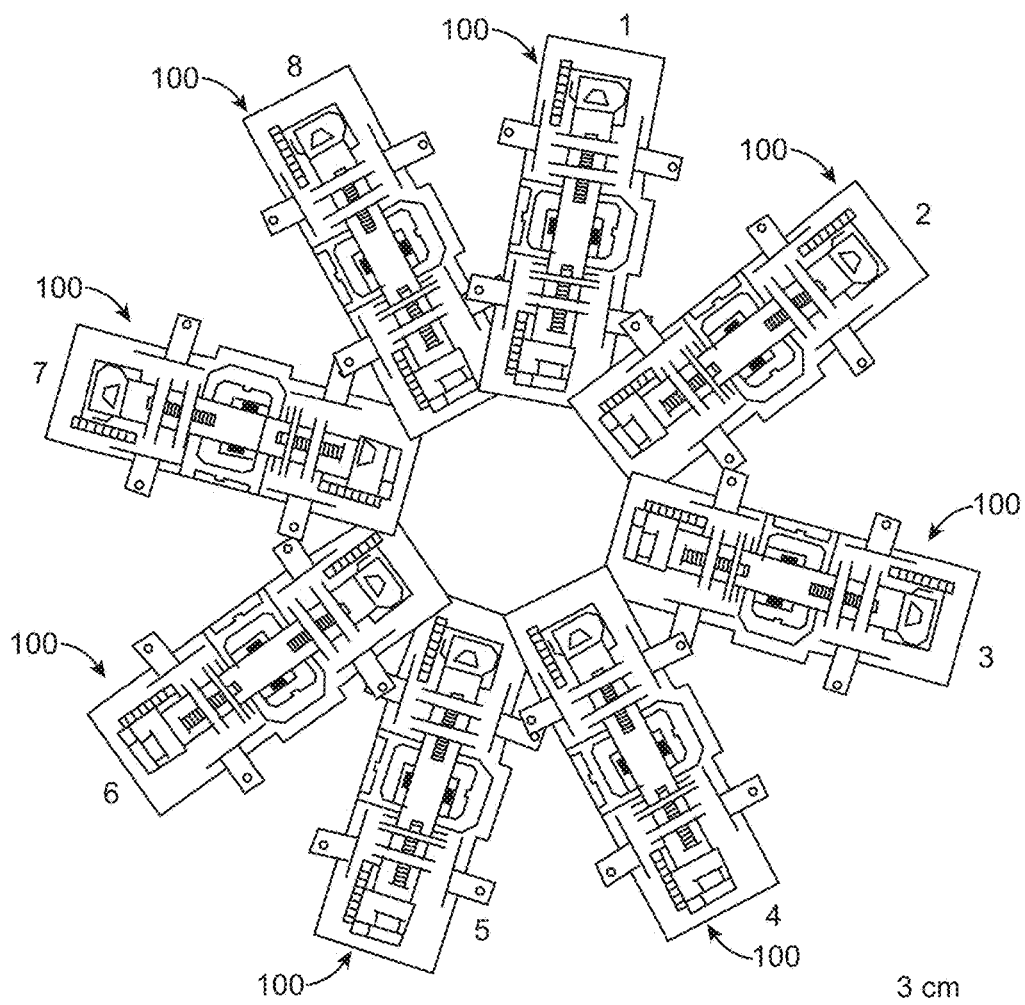
FIG. 3 illustrates different embodiments of optical microscopes.
Figure 4:
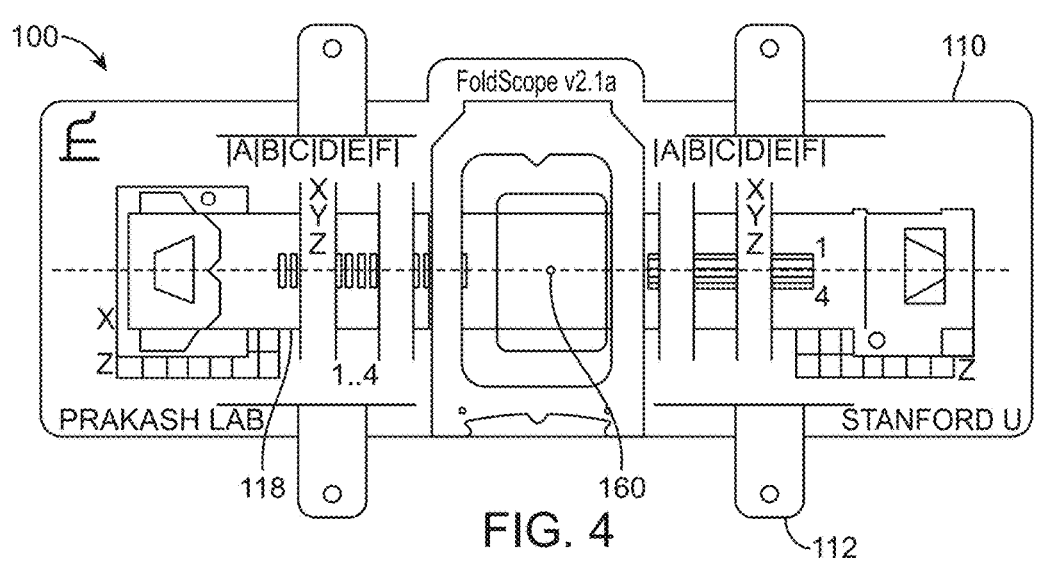
FIG. 4 illustrates an optical microscope in accordance with an embodiment.

FIG. 3 illustrates different embodiments of optical microscopes with various magnifications and modalities. Bright field optical microscopes are shown with a magnification of 435× (1), 1450× (2), and 2175× (3). A fluorescence microscope with Acridine Orange and Auramine stains is depicted in 5. A polarization microscope is shown in 6. An optical microscope with a multi-array of lenses is shown in 7. A projection microscope is shown in 8. FIG. 4 illustrates an optical microscope in accordance with an embodiment assembled from a flat material.

Figure 5A:
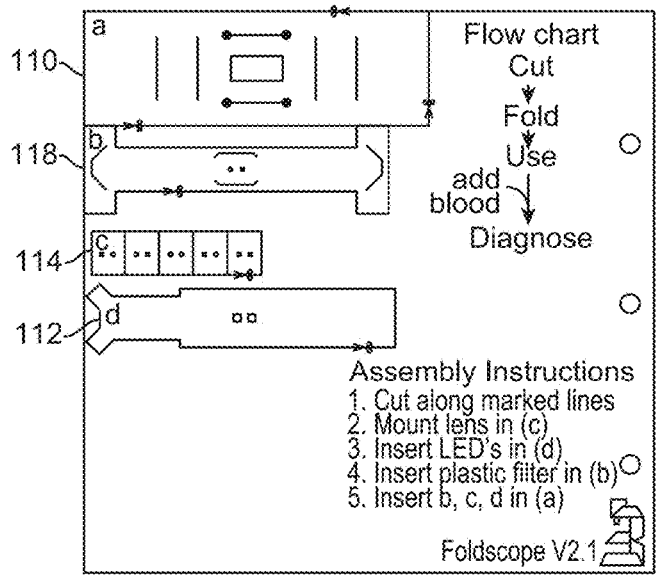
FIGS. 5A-E illustrate schematic examples of optical microscopes at various assembly stages.
Figure 5E:
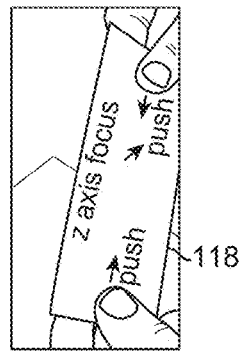
Figure 5B:
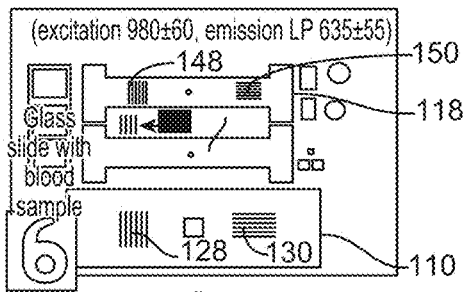
Figure 5C:
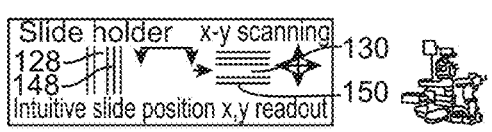

FIG. 5A shows a schematic arrangement of the parts of an optical microscope on a flat material that can be cut, folded, assembled, and used to diagnose a blood sample. FIG. 5B illustrates various parts of an optical microscope prior to assembly in accordance with an embodiment. FIGS. 5C, 5D, and 5E illustrate assembling and adjusting portions of an optical microscope. FIG. 5C illustrates the x-y scanning feature. FIG. 5D illustrates two lenses 160 with magnifications of 140× and 330×, respectively. The 140× magnification lens 160 produces a bright field image. The 330× magnification lens 160 produces a fluorescence image. The glass slide 170 is shown engaged with the optical microscope 100. FIG. 5E illustrates the z-axis focus by pushing inward on the edges of the optical stage.

Figure 5F:
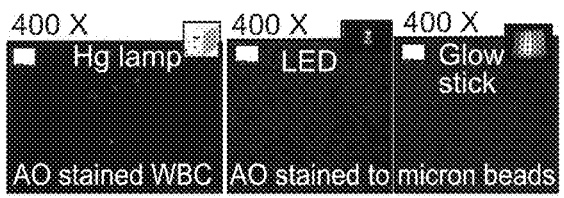
FIGS. 5F-G are various images produced by a conventional microscope compared to images taken with an optical microscope in accordance with embodiments.
Figure 5D:
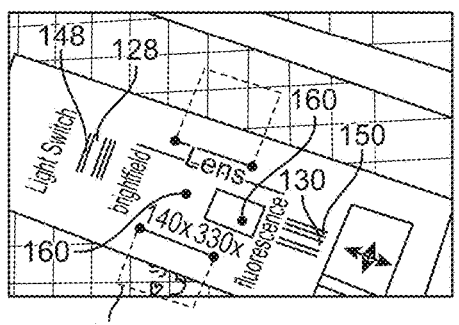
Figure 5G:
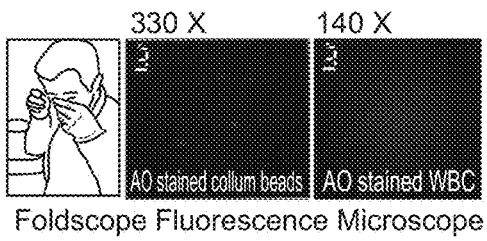

FIGS. 5F-G are various images produced by a conventional microscope (FIG. 5F) compared to images taken with an optical microscope in accordance with embodiments (FIG. 5G). The images in FIG. 5F were taken using a Nikon Eclipse fluorescence microscope with a Hg lamp, LED, and glow stick under a magnification of 400×, respectively. FIG. 5G illustrates fluorescence images produced by an optical microscope in accordance with embodiments disclosed herein for AO stained beads and AO stained white blood cells at a magnification of 330× and 140×, respectively. The images illustrated in FIG. 5F are comparable to the images achieved using a conventional microscope shown in FIG. 5G.

Figure 6B:
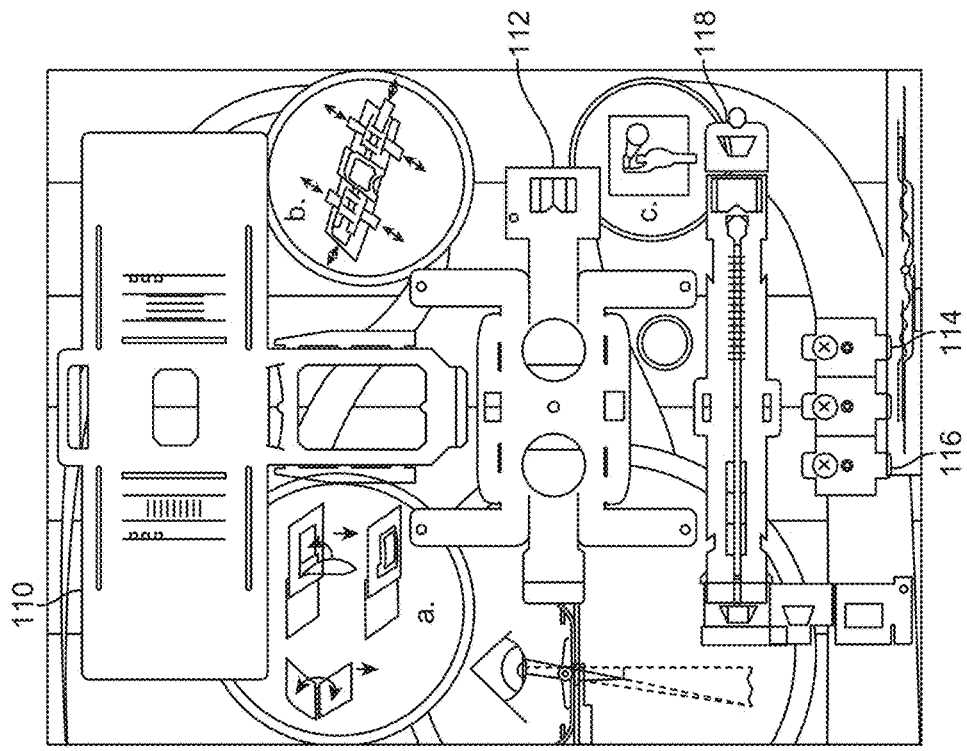
FIGS. 6A and 6B illustrate examples of optical microscopes prior to folding in accordance with various embodiments.
Figure 6A:
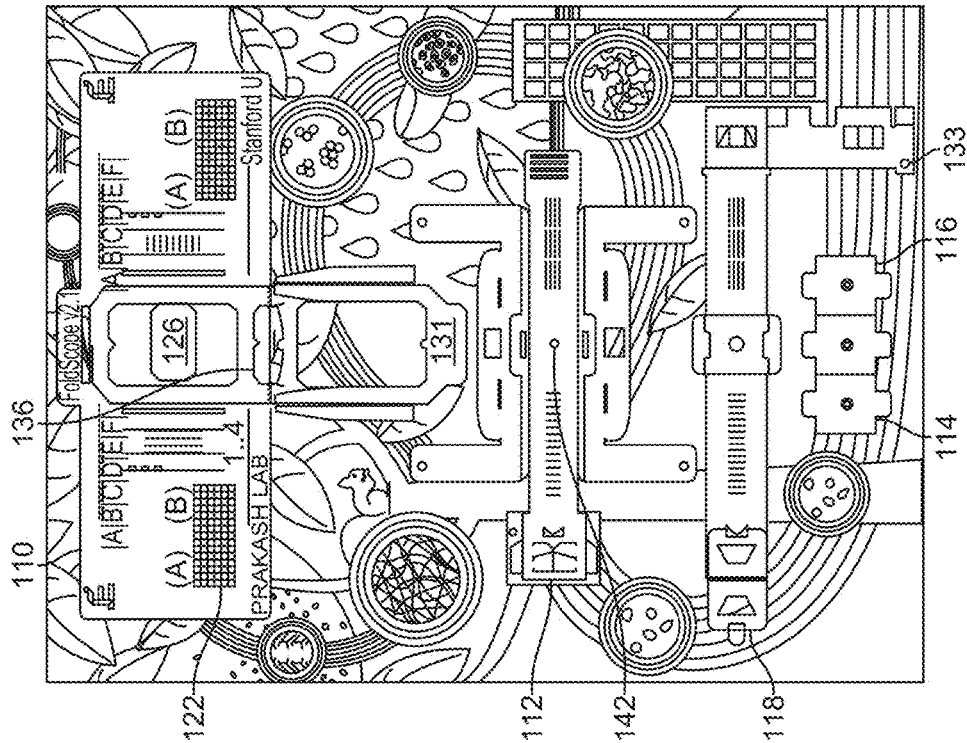

The optical devices disclosed herein can be assembled without written language instructions. This is advantageous because the optical microscopes can be used in a variety of countries without requiring translations of the instructions for different countries. The language free folding instructions can include colors and pictures to facilitate the assembly of the optical microscope. The language free instructions can be directly printed on the instrument itself, for example a color matching scheme that guides a user to correct folding sequence. The surfaces of the optical microscope can also provide staining instructions for the sample. The surfaces of the optical microscope can include an identification guide for the diagnostics provided on the optical microscope. FIGS. 6A and 6B illustrate examples of optical microscopes prior to folding in accordance with various embodiments. FIGS. 6A and 6B are illustrated in black and white but can include bright colors to facilitate the folding and assembling instructions.

Figure 7A:
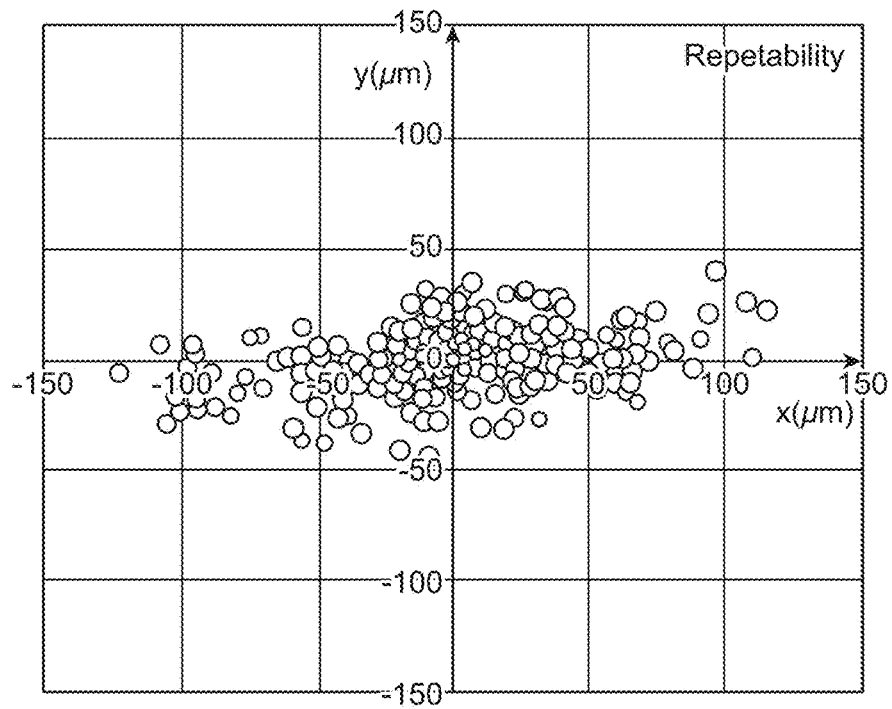
FIGS. 7A and 7B illustrate data for the accuracy and repeatability, respectively, for folding and unfolding an optical microscope in accordance with embodiments.
Figure 7B:
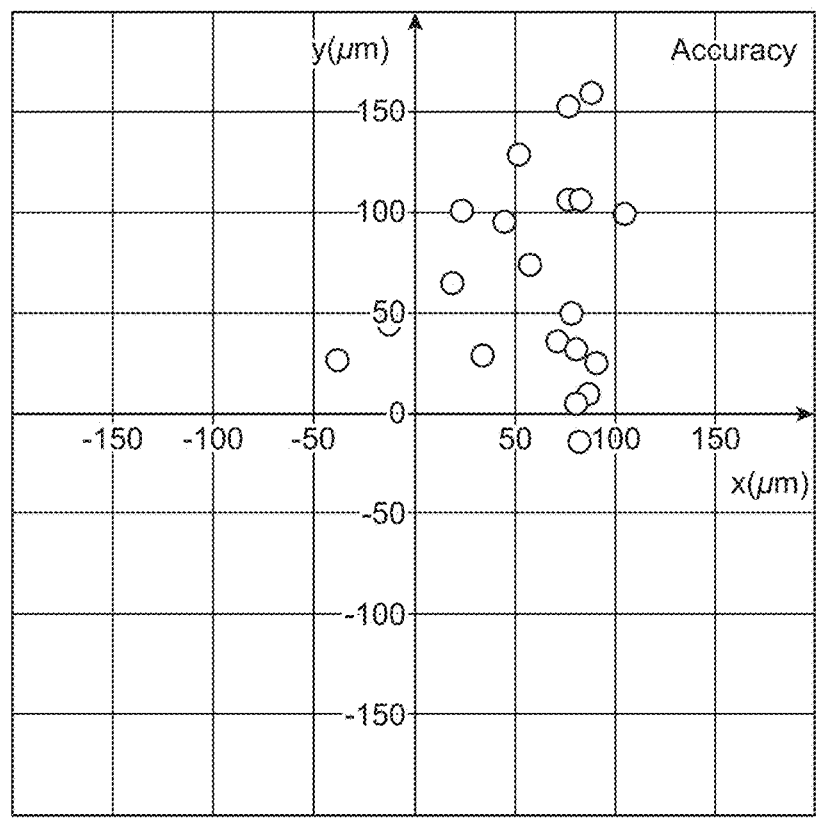

The optical microscopes can be folded and assembled with a high degree of precision and accuracy. Traditional optical instruments require significant alignment post assembly. An advantageous feature of a folding optical assembly design is that self-alignment can be exploited with kinematic constraints present in how the folds are executed, even for manual folding. Folding a sheet of paper introduces an alignment error proportional to the thickness of the paper in a valley or mountain fold. This error arises from uncertain position of a hinge in a fold due to buckling of paper in the inner edge of the fold. The alignment errors can be corrected by introducing folding features that provide kinematic constraints, for example mating the two stages and implementing closed structural loops during folding. For a mechanical process, repeatability is inversely proportional to the square root of contact points for elastically averaged coupling alignment schemes. The optical microscopes disclosed herein, for example, can utilize four contact points and two alignment surfaces to couple the optics and illumination stage. To characterize the alignment accuracy and repeatability of the optical microscopes, twenty independent microscopes were cut out of A4 sheets of paper with a laser cutting tool having a cutting error of ±6 microns. Each microscope was hand folded and unfolded repeatedly, while measuring X-Y alignment errors between the optical and illumination stage. FIGS. 7A and 7B illustrate data for the accuracy and repeatability, respectively, for folding and unfolding the optical microscopes. Assembly accuracy and precision for the optical alignment as small as 10 microns was demonstrated for the microscope components in a manual assembly process using paper with a thickness of about 150 μm. The optical alignment can include the alignment of the light source, optic/lens, sample stage, and any other items within this path, such as filters, diffusers, apertures, etc. The alignment precision was acceptable for the lens sizes disclosed herein, for example a lens having a diameter of 300 μm.

Figure 25A:
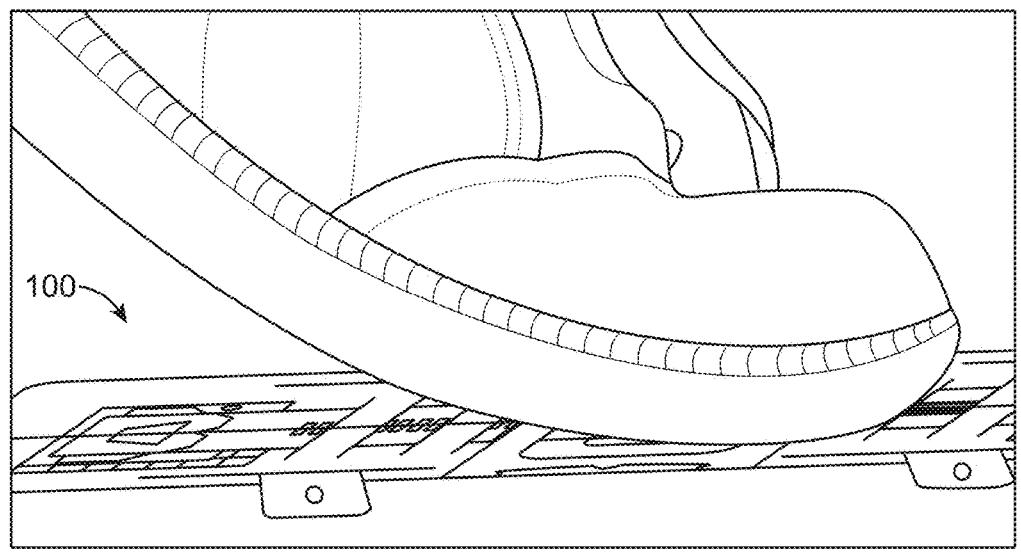
FIG. 25A is a schematic illustration of a person stepping on a single ball lens optical microscope.
Figure 25B:
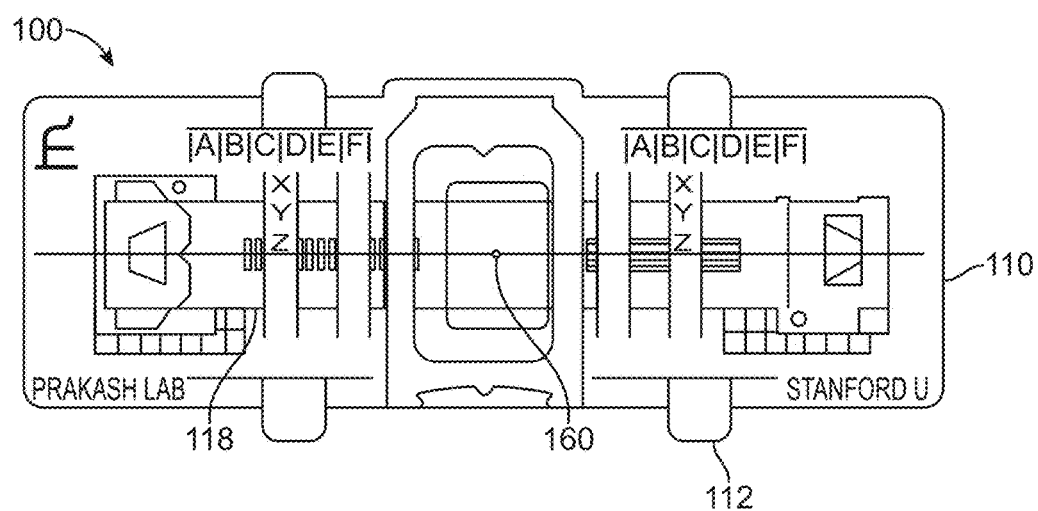
Figure 26:
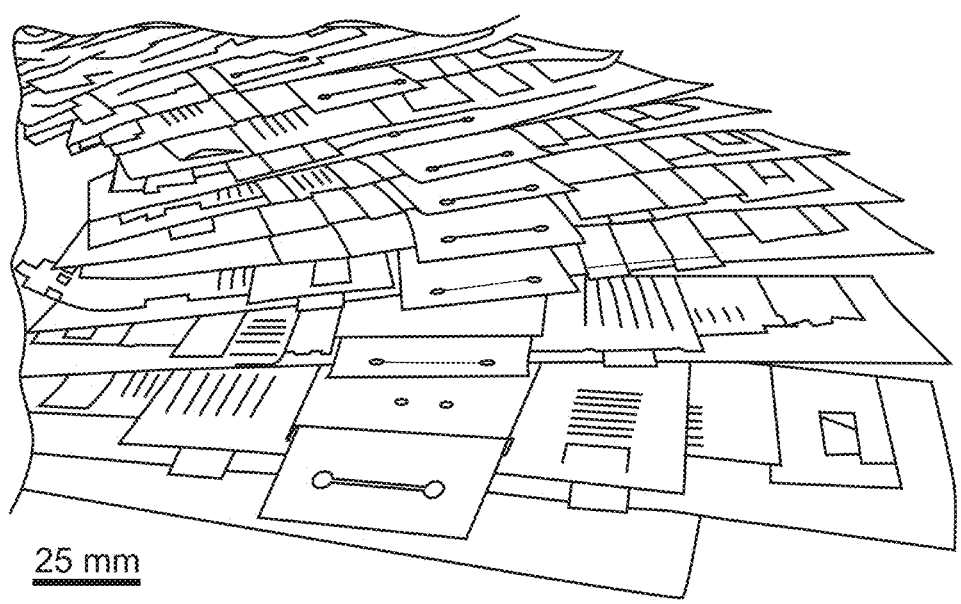
FIG. 26 illustrates optical microscopes cut using a laser in accordance with embodiments.

The optical microscopes disclosed herein can be durable and resistant to outdoor elements. For example, the optical microscopes can be stepped on and still work as shown in FIGS. 25A-B. The microscopes can work submerged in water and survive a fall from a three story building.

The optical device can be optimized based on the desired application or for general use. A number of parameters can be adjusted to optimize the optical device. For example, the lens size and shape, lens refractive index, lens material, the optical path length, optical path shape/direction, the lens aperture size and shape, the light source type and location, the aperture associated with the light source, the light source intensity and profile, the alignment of the light source with the lens, the wavelength of the light source, the polarization and coherence of the light source, the magnification of the sample, the resolution of the image, the inclusion of additional features such as automated staining or sample separation, the inclusion of a cell counter feature for keeping track of the level of parasitimia, optical filters placed in front of the light source or in front of the lens, etc.

In some embodiments, the folding accuracy is accomplished by geometrical features cut in flat material that act as kinematic couplings thus providing a self-alignment. In some embodiments, self-alignment is further improved by providing structural closed loops in folding steps.

In some embodiments, the optical microscope can have an integrated microfluidic channel for bringing samples directly to the microscope lens.

In some embodiments, the optical microscope can be incinerated after one use safely and thus can be used with infected samples. In some embodiments, the entire microscope is disposable after single or multiple uses.

In some embodiment, a waveguide is utilized to channel light from the light source to other optical components.

In some embodiments, the sample is reacted to a reagent already deposited in the sample holding stage via a microfluidic network embedded in the sample holding stage. In some embodiments, the reagent is dried for preservation. In some embodiments, the reagent is wet.

The devices disclosed herein can be modified to modify the optical path to a desired configuration. The flexibility in designing the optical path allows the device to be used as a general purpose optical design tool. Optical devices such as microscopes, interferometers, and spectrophotometers can be assembled using the methods, devices, and concepts disclosed herein.

In some embodiments, the lens can be cleaned by inserting a slide with lens paper attached to the surface followed by panning the second stage with the lens/optic in circles over the lens paper so that the lens paper brushes off contaminants from the surface of the lens.

FIG. 8A illustrates an exemplary optical path of an optical microscope in accordance with an embodiment. FIG. 8A illustrates the distance between the light source (e.g. LED) and sample object as $D_{led-obj}$, the distance between the sample object and lens as $D_{obj-lens}$, the distance between the lens and image plane as $D_{lens-img}$. The optical chain of the optical microscope includes illumination sources (distance $D_{led-obj}$), condenser lens, illumination aperture ($A_1$) sample glass slide, spherical micro-lens (radius r, refractive index n at a distance $D_{obj-lens}$ from the slide) and entrance ($A_2$) and exit ($A_3$) aperture. For a real image in projection mode, the image plane is a distance $D_{lens-img}$ apart. The total optical path length from the light source to the last lens surface can be about 2.5 mm, which is only about 1% of the optical path length for a conventional microscope. The decreased optical path length allows for the microscope to be constructed with a short vertical height assuming a vertical optical path. The reduced optical path length can also minimize the extent to which stray light can enter the system and degrade optical performance.

Figure 9B:
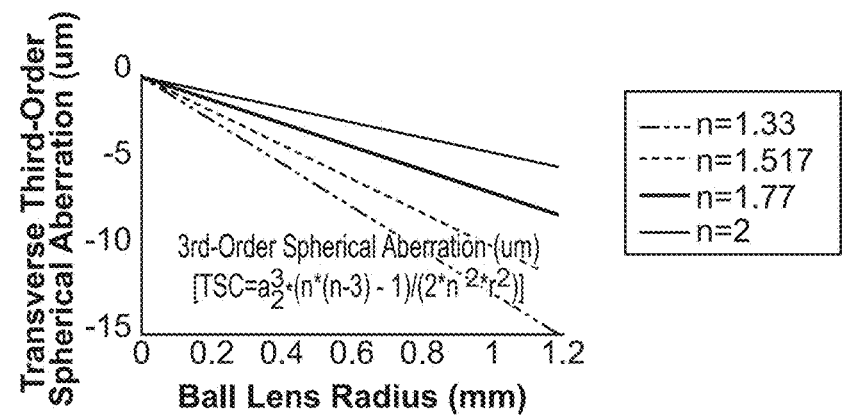
FIG. 9B illustrates the third order spherical aberration versus ball lens radius.

FIG. 9A illustrates the magnification obtained versus various lens radii for different refractive index values. FIG. 9A depicts overall magnification obtained as a function of ball radius (r) for refractive index (n) values ranging from 1.33 to 2. The parameters shown in FIG. 9A can be optimized to improve the resolution of the optical microscope. Utilizing ray-tracing methods, a collimated beam of light entering an aperture diameter $A_2$ and a spherical ball lens with a diameter (D=2r) and refractive index n, is focused to a point given by the effective focal length $$EFL = \frac{nr}{2(n-1)}$$

and numerical aperture (NA) is given by $$NA = \frac{A_2(n-1)}{nr}$$

with magnification inversely proportional to ball lens radius as shown in FIG. 9A. A magnification of ~2175× can be obtained with a sapphire glass lens of about 200 μm in diameter as shown in FIG. 9A. FIG. 9B illustrates the third order spherical aberration versus ball lens radii. The transverse third order spherical aberration can be expressed as $$TSC = \frac{[n(n-3)+1]A_2^3}{2n^2 r^2}$$

which reduces as a function of ball lens radius as shown in FIG. 9B.

Figure 10:
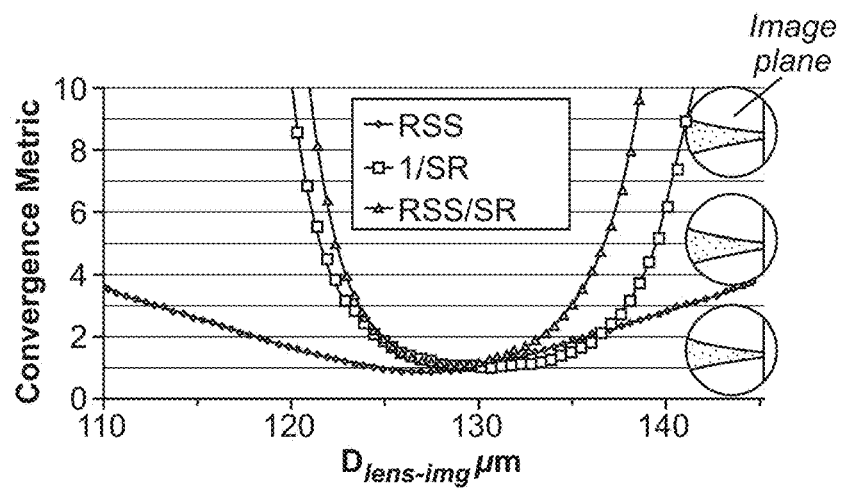
FIG. 10 illustrates focusing metric versus the distance between the lens and image for RMS spot size (RSS), inverse Strehl ratio (1/SR), and ratio of spot size to Strehl ratio (RSS/SR).

The aperture radius ($A_2$) can be optimized to maximize contrast and resolution, for example by balancing spherical aberration in the image and transmitted illumination intensity for a fixed wavelength of light. Considering collimated incident light, resolution as a function of lens-image distance ($D_{lens-img}$) and aperture radius ($A_2$) can be calculated both numerically and analytically. Since the optimization depends on two independent parameters numerical optimization is achieved in two stages. The first stage optimizes the focus by varying $D_{lens-img}$, while the second stage optimizes the resolution by varying $A_2$ with $D_{lens-img}$ equal to its optimum value for each aperture radius. For the first optimization stage, the focusing metric is chosen to be the reciprocal of the Strehl Ratio (1/SR). Minimizing this focusing metric effectively selects a value for $D_{lens-img}$ corresponding to diffraction focus, or best focus. FIG. 10 illustrates focusing metric versus the distance between the lens and image for RMS spot size (RSS), inverse Strehl ratio (1/SR), and ratio of spot size to Strehl ratio (RSS/SR).

Figure 11A:
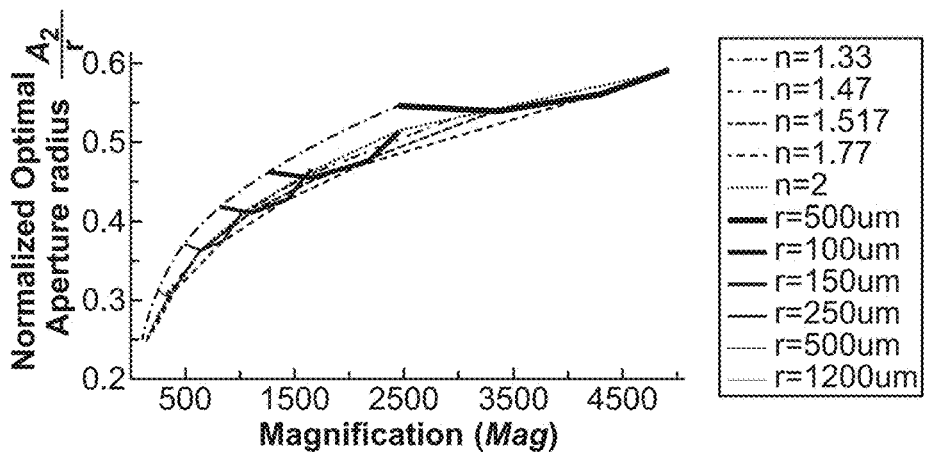
FIG. 11A illustrates the normalized optical aperture radius versus magnification for various radii and refractive index values.
Figure 11B:
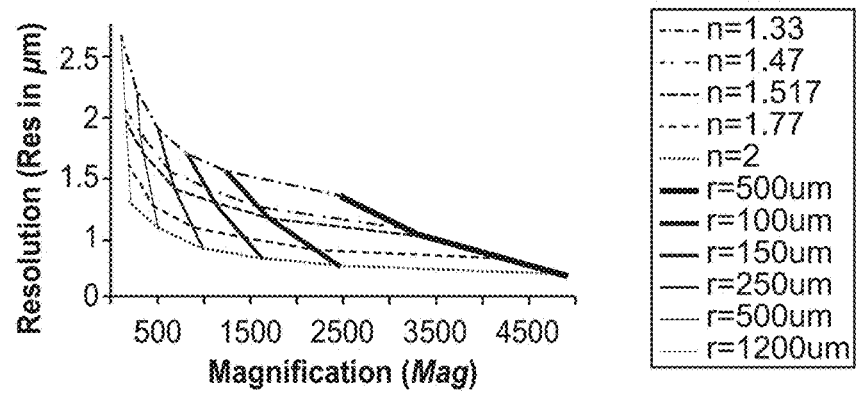
FIG. 11B illustrates the resolution versus magnification for various radii and refractive index values.
Figure 12A:
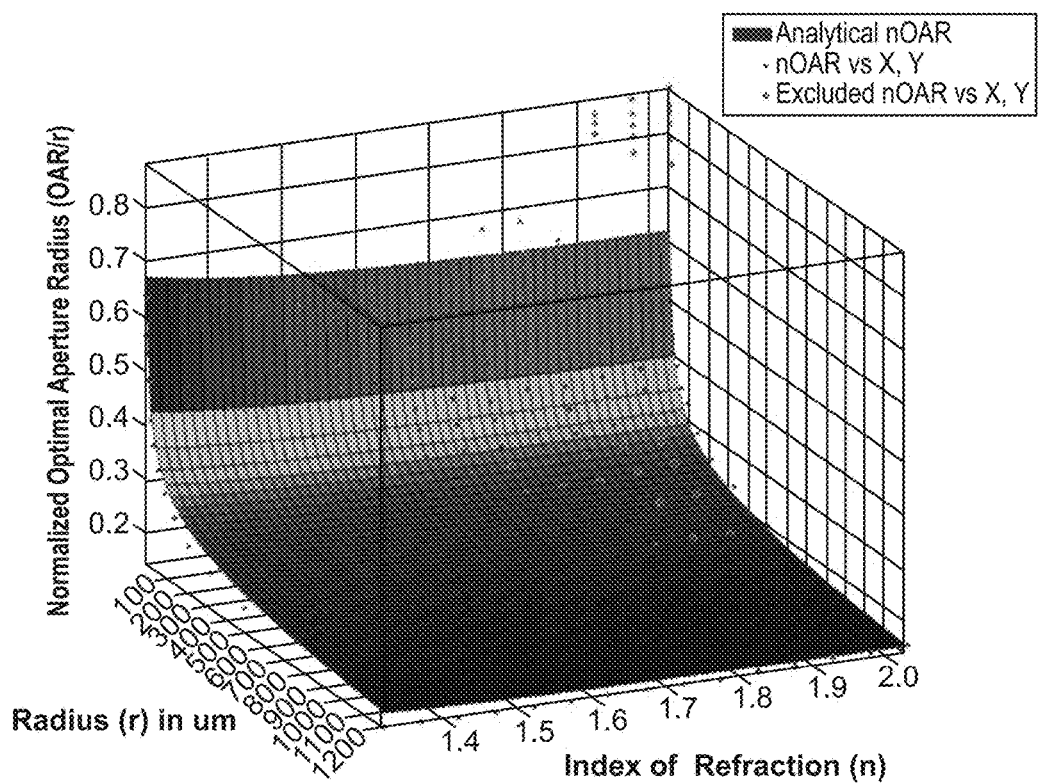
FIGS. 12A-12B illustrate calculations for the optimal aperture radius and resolution, respectively, as a function of lens radius, refractive index, and incident light wavelength.
Figure 12B:
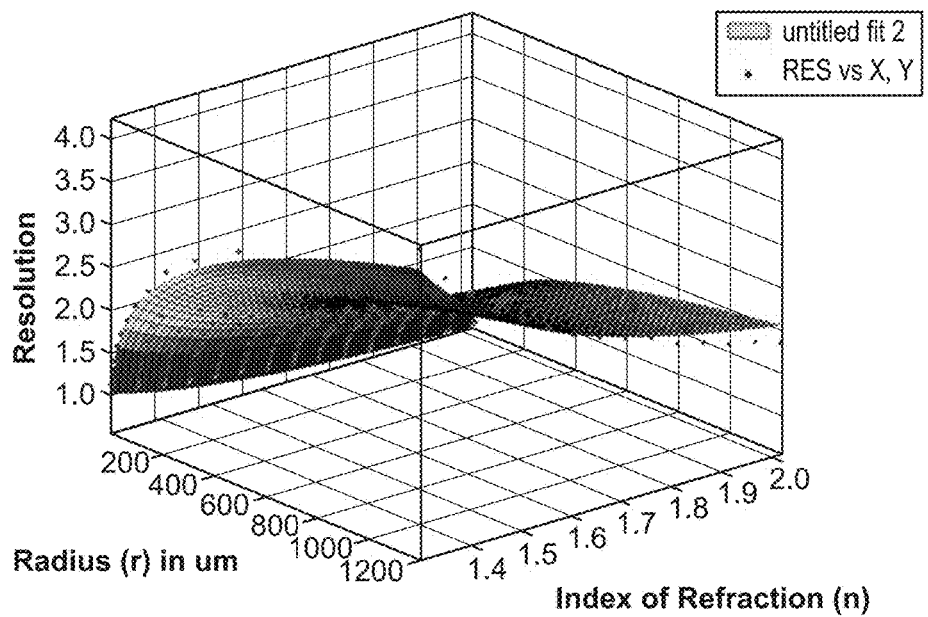

The second optimization stage calculates optimal aperture diameter ($A_2$) by minimizing a resolution metric, evaluated as the ratio of Airy Disk Radius and Strehl Ratio (ADR/SR). Graphically, this metric gives a curve that subtends the Airy Disk Radius (ADR) for small aperture radii and parallels RMS Spot Size for large aperture radii. Also, it provides good numerical convergence. Numerical modeling results in design curves as a function of lens radius r, refractive index n, and incident light wavelength λ. FIG. 11A illustrates the normalized optimal aperture radius versus magnification for various radii and refractive index values. FIG. 11B illustrates resolution versus magnification for various radii and refractive index values. FIGS. 12A-12B illustrate calculations for the optimal aperture radius and resolution, respectively, as a function of ball lens radius, refractive index, and incident light wavelength.

For the analytical model, the optimization proceeds by evaluating the diffraction limited resolution at best focus, where the normalized longitudinal aberration (A) is equal to 1. Two different analytical models can be used to derive identical results, within a multiplicative constant. In the first analytical model, Airy Disk Radius is equated to RMS Spot Size (ADR=RSS). The Airy Disk Radius is evaluated as ADR=1.22·λ·F, where F=EFL/2$A_2$ is the focal ratio or F/#. The RMS Spot Size is approximated as the RMS blur radius ($r_{RMS}$), at best focus, RSS=4F·|S|/√6, where F is the focal ratio, S=s·$A_2^4$ is the peak aberration coefficient and s is the aberration coefficient. For a ball lens, the following expression was derived for the aberration coefficient: s=−(n−1)·[n+(2−n)·(2n−1)]/8$r^3 n^3$. Setting the expression for ADR equal to the expression for RSS and solving for $A_2$/r, the following expression is obtained for the normalized optimal aperture radius:

$$nOAR = k_1' \cdot \left( \frac{\lambda \cdot n^3}{r \cdot (n-1) \cdot [n+(2-n) \cdot (2n-1)]} \right)^{\frac{1}{4}},$$

where $k_1'$=(1.22·2·√6)$^4$≅1.5636. This can be substituted into the expression for ADR (or that for RSS) to obtain the following expression for image resolution:

$$RES = k_2' \cdot \left( \frac{\lambda^3 \cdot r \cdot n \cdot [n+(2-n) \cdot (2n-1)]}{(n-1)^3} \right)^{\frac{1}{4}},$$

where $k_2'$=(1.22$^3$/2√6)$^{1/4}$≅0.1951. The above expression for optimal aperture and corresponding resolution show good agreement with the numerical calculations illustrated in FIGS. 12A-B. The second analytical model determines the diffraction-limited resolution by minimizing the ratio of Airy Disk Radius (ADR) to Strehl Ratio (SR), i.e. by solving ∂/∂a (ADR/SR)=0. For this model, the Strehl ratio can be expressed using the empirical approximation, SR=exp[−(2π$ω_s$/λ)$^2$], where $ω_s$ is the RMS wavefront error at best focus. As mentioned earlier, this model produces the same results as the first model, except with the constants now being, $k_1'$=(6√10/π)$^{1/4}$≈1.5677 and $k_2'$=(1.22/4)·(π/6)$^{1/8}$≅(e/10)$^{1/8}$≅0.2205. For example, the numerical and analytical models predict an optimized image resolution of about 0.88 um for a 300 um diameter sapphire lens, which agrees well with experimental data (see FIG. 12B and FIG. 18). In some embodiments a resolution can be as high as 500 nm at magnifications greater than about 2000×.

The resolution of the optical microscope can be quantified by observing an object having a known size. For example, fluorescence resolution was determined between two adjacent microspheres using Imager s linear intensity profile tool. Microspheres were considered to be resolvable when the minimum intensity value between the two spheres was 84.4% of the maximum intensity of the normalized dataset as is in accordance to the Rayleigh Criterion. To make peaks of intensity distinguishable, a local polynomial regression model weighted across every 10 pixels was used to smooth the data. Using this analysis, the 1 µm beads were barely resolvable. FIG. 18 illustrates an image of 1 µm polystyrene beads using a 300 µm ball lens and an aperture size of about 150 µm. FIG. 19A illustrates a bright field image of 1 micron polystyrene beads. FIG. 19B illustrates a fluorescent image of 2 micron polystyrene beads. FIG. 19C illustrates a plot of intensity versus distance.

For brightfield resolution, the beads could clearly be resolved between one another as shown in FIG. 18. As there are several methods for measuring resolution in brightfield, we borrowed a technique used by Lorusso and Joy (2003) for quantifying resolution using the Fourier Transform of the bead-matrix image. FIG. 19D is an image of the polystyrene beads shown in FIG. 18 along with a 2D-Fourier transform showing the power spectrum of the threshold image and spatial frequency detail. A threshold was set for the original image such that noise was removed and the 2-dimensional fast-Fourier transform was then performed on the image. Upon taking the power spectrum of the Fourier transform, the extent of the spatial frequencies was found. The mean radius of this ellipsoidal extent was then used to calculate the smallest feature size, which is equal to the resolution, in the image using the following equation: Resolution=ROIW*PixelSize/RFFT*Image Scaling where ROIW is the average width of the sensor and RFFT is the average radius of the power spectrum in the Fourier domain. The pixel size is the size of the pixels on the CCD. The image scaling is a factor used in determining the scale of the image plane compared to the CCD plane. For this image, the ROIW was 4680 pixels, the RFFT was 318.25, the Pixel Size was 6.4 micrometers and the Scaling factor was 95 CCD pixels per object pixel. This resulted in a calculated resolution of 0.99 micrometers. In general, this is a conservative method of measuring resolution as the smallest features can be filtered out with the noise during the threshold step.

Figure 13:
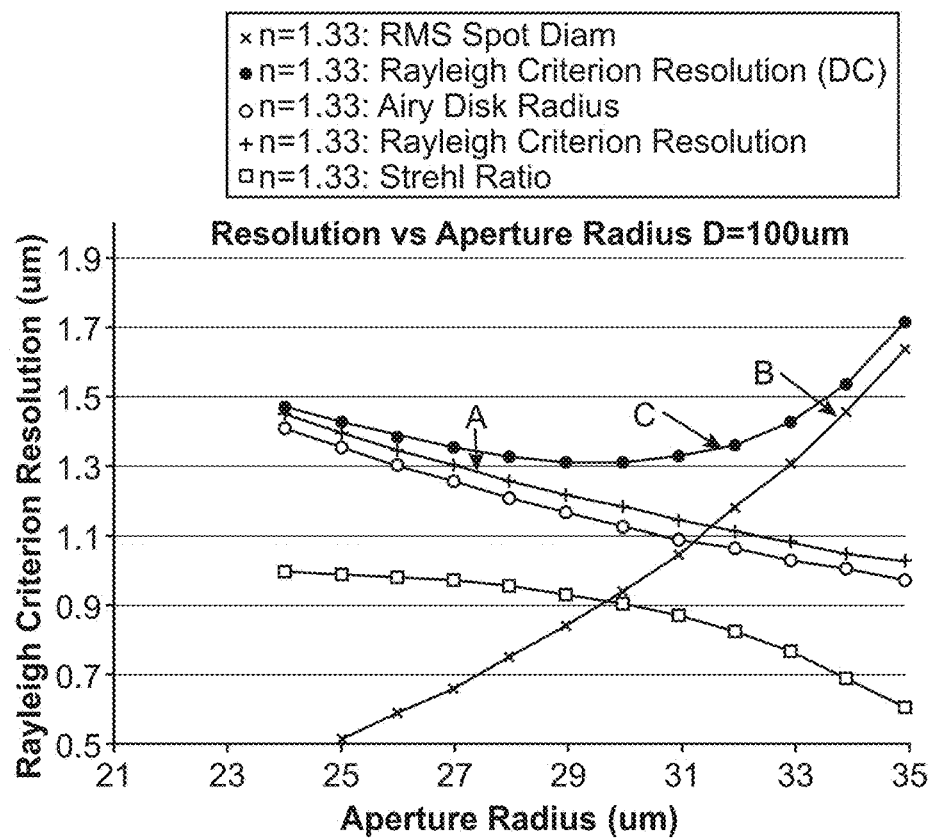
FIG. 13 is a graph of resolution versus aperture radius for various metrics.
Figure 14:
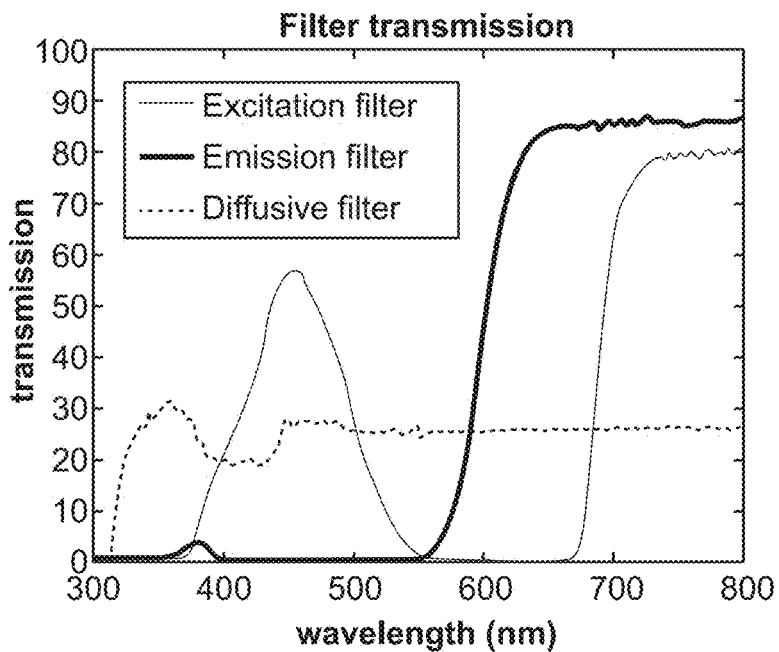
FIG. 14 is a graph of the filter transmission versus wavelength for various filter types.
Figure 23:
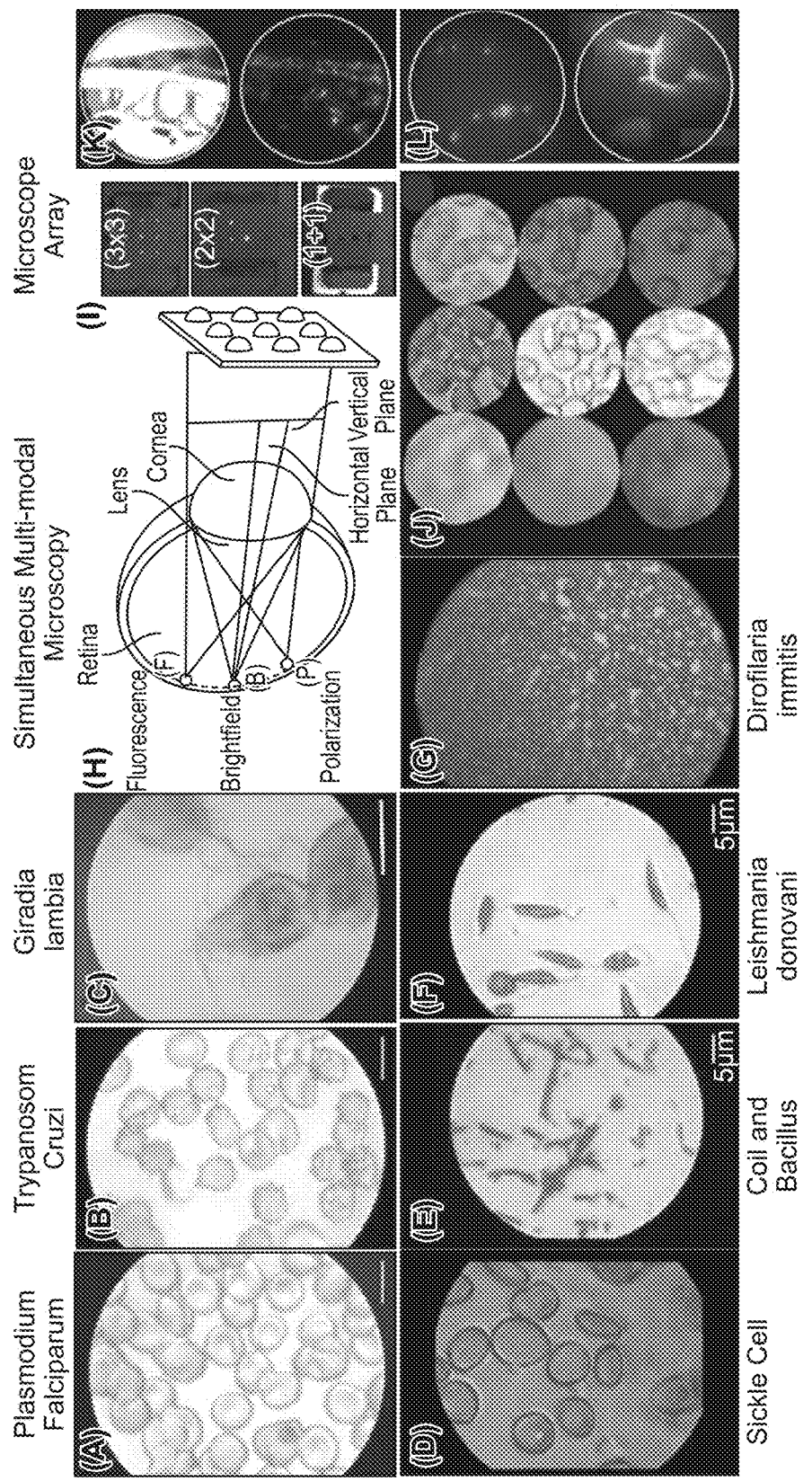
FIG. 23A is an image produced by a single ball lens optical microscope in accordance with an embodiment of a ring stage malaria parasite *Plasmodium Falciparum* in a thin blood smear stained with Giemsa blue.
FIG. 23B is an image produced by a single ball lens optical microscope in accordance with an embodiment of *Trypanosom Cruzi* in thin blood smear stained with Giemsa.
FIG. 23C is an image produced by a single ball lens optical microscope in accordance with an embodiment of Giardia stained with Giemsa.
FIG. 23D is an image produced by a single ball lens optical microscope in accordance with an embodiment of sickle-shaped red blood cells.
FIG. 23E is an image produced by a single ball lens optical microscope in accordance with an embodiment of gram positive and gram negative bacteria.
FIG. 23F is an image produced by a single ball lens optical microscope in accordance with an embodiment of *Leishmania donovani* stained with Giemsa.
FIG. 23G is an image produced by a single ball lens optical microscope in accordance with an embodiment of Burgia XX stained with Giemsa in a thin blood smear.
FIG. 23H is a schematic illustration of a 3×3 lens array with different modalities embedded in an optical microscope in accordance with an embodiment.
FIG. 23I illustrates a portion of microscopes with nine (3×3), four (2×2), and 2 parallel optical paths in accordance with various embodiments.
FIG. 23J are bright field images of human blood cells produced by an optical microscope in accordance with an embodiment produced by a 3×3 array of lenses FIG. 23K are images produced by a single ball lens optical microscope in accordance with an embodiment of a pine seed using bright field and polarization microscopy, respectively.
FIG. 23L are images produced by a single ball lens optical microscope in accordance with an embodiment of multi-fluorescence images of 2 μm polychromatic beads.

FIG. 13 is a graph of resolution versus aperture radius for various metrics. The optimal resolution metric was obtained using the ratio of Airy Disk to Strehl ratio. FIG. 14 is a graph of the filter transmission versus wavelength for various filter types. FIG. 14 compares an excitation filter, emission filter, and diffusive filter. Associated fluorescence image data using the above filter set as barrier (blue) and emission (red) filter is shown in FIG. 18 and FIG. 23L. In some embodiments the filters can be provided with separate light sources. In some embodiments the filters can be integral with the sample stage. In some embodiments the filter can be included with the optic stage.

Figure 15A:
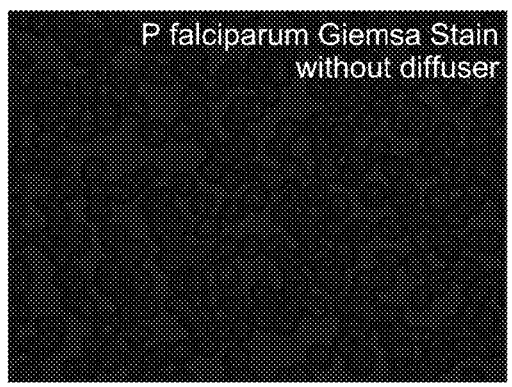
FIGS. 15A and 15B are images of malaria samples observed with and without a diffuser.
Figure 15B:
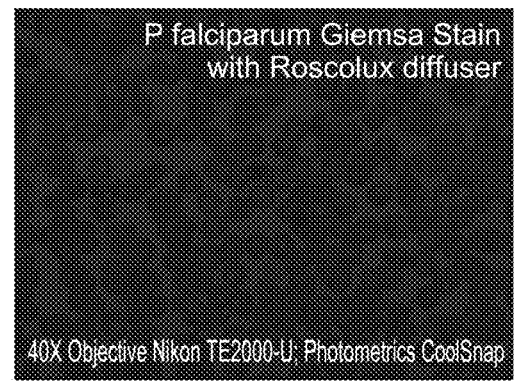

Malaria samples are often observed under an oil immersion lens due to ring artifacts that arise because of curved shape of a red blood cell. FIGS. 15A and 15B are images of malaria samples observed with a diffuser. FIG. 15A is an image obtained using an embodiment of the optical microscopes described herein and FIG. 15B is an image obtained using a conventional microscope. FIGS. 15A and 15B illustrate that good quality images can be obtained without the use of an oil immersion lens. Using a simple thin plastic film diffuser that cuts out directional illumination can remove artifacts due to cell inhomogeneity and enhance the image component due to light absorption. An example of the transmission spectra of the diffusive filter is shown in FIG. 14.

Figure 16A:
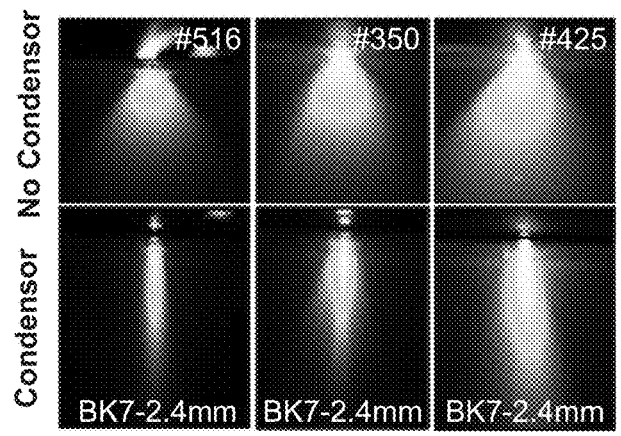
FIG. 16A illustrate three different LED light sources with and without a condenser.
Figure 16B:
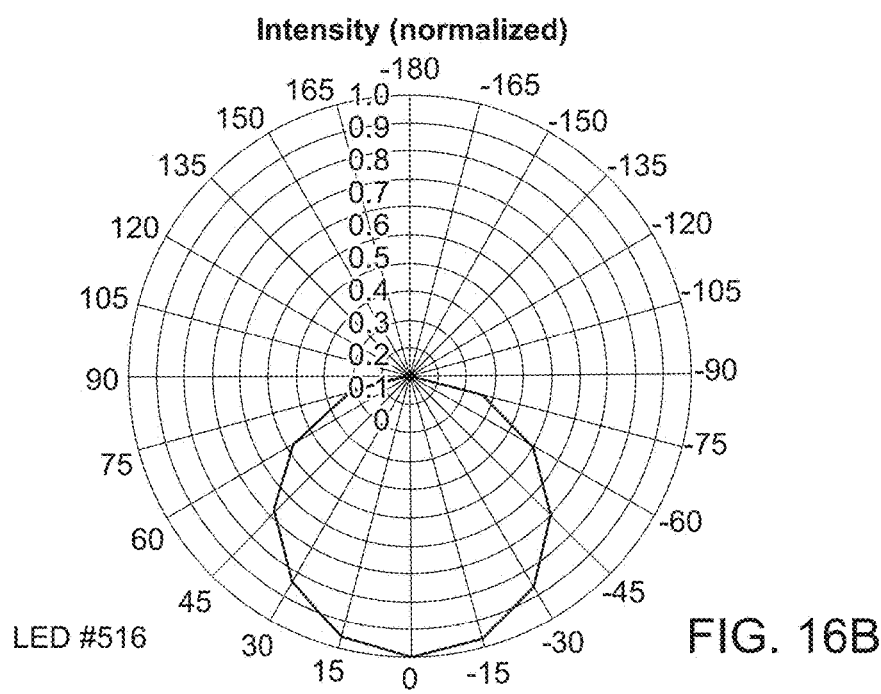
FIG. 16B illustrates the intensity of a LED light source.

FIG. 16A illustrate three different LED light sources with and without a condenser. The three LED based light sources, labeled #516, #350 and #425, were imaged using fluorescein dissolved in water. As shown in FIG. 16A, the condenser further focuses the light. FIG. 16B illustrates the illumination intensity in a polar plot of LED light source #516.

Figure 17A:
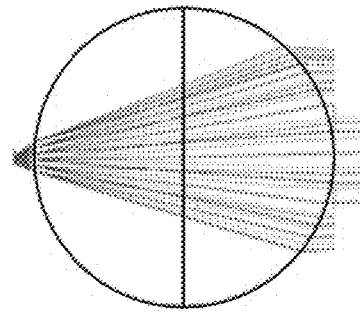
FIG. 17A is a model of the ray tracing for a 0.3 mm spherical ball lens.
Figure 17B:
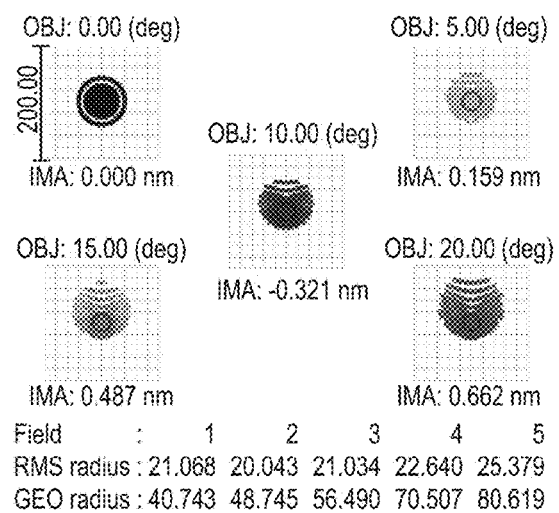
FIG. 17B a model of the RMS spot size for off-axis rays.
Figure 17C:
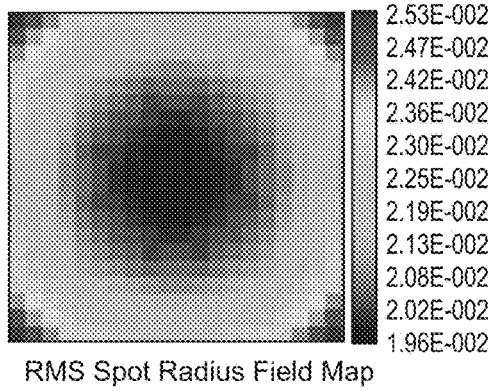
FIG. 17C is a model of an RMS spot radius field map.
Figure 17D:
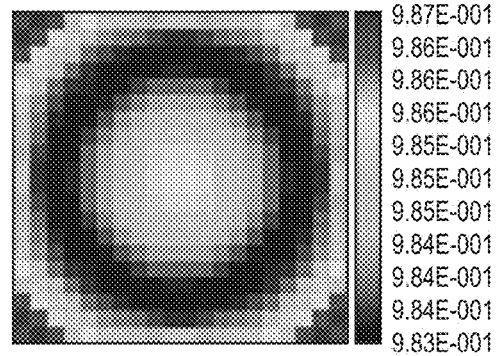
FIG. 17D is a model of a Strehl Ratio field map.

Additional modeling is shown in FIGS. 17A-D. A 0.3 mm sapphire lens is modeled in FIGS. 17A-D. FIG. 17A is model of the ray tracing for a 0.3 mm spherical ball lens. FIG. 17B a model of the RMS spot size for off-axis rays of 0, 5, 10, 15, and 20 degrees. FIG. 17C is a model of an RMS spot radius field map. FIG. 17D is a model of a Strehl Ratio field map.

Figure 8B:
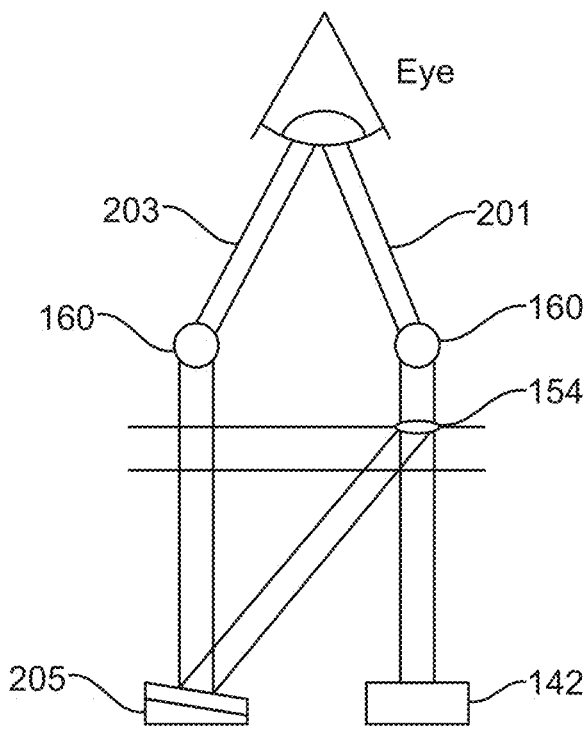
FIG. 8B is a schematic illustration of an optical path for an optical microscope in accordance with an embodiment.

The microscope may also allow a user to view the same object at two different magnifications at the same time. This embodiment can provide two concentric magnification regions, where the inner region is at a higher magnification than the outer region. This may be achieved by placing a half ball lens above a smaller diameter ball lens in a doublet configuration, for example. The microscope may be utilized as a single purpose microscope, having optics that depend on the type of stain used, the light source and the filters used. The optics design allows for illumination to track with the optics. A reflective mylar sheet may be implemented for providing a mirror surface, and may allow for simultaneous frontside/backside imaging as shown in FIG. 8B.

The present microscope may have a simultaneous multi-modal imaging feature. Multi-modal may involve two or more images on the retina simultaneously by taking advantage of the psychophysics of the eye. The present microscope may have one or more lenses. Each of the one or more lenses may correspond to a different microscope modality. The microscope modalities may include brightfield, darkfield, fluorescence in many sets depending on the type of filter implemented (GFP, YFP, AO, Auramine-O, DAPI, or other filter) or any other filter, and polarization using polarization filters and any other optical microscopy. Each of the microscope modalities may be implemented at high and low magnifications. One or more of the microscope modalities may be implemented at the same time on optical microscope 100 in any arrangement. For example, the microscope may include darkfield imaging at a specific magnification and brightfield imaging at a second magnification. Hence, in the same field of view, the user may be looking at the same object 1000× magnified, and simultaneously looking at it 10× magnified. In various embodiments, the microscope modalities form an array.

In various embodiments, the ball lenses may be arranged in an 3×3, 4×4 or 5×5 matrix, where each lens provides identical images but with a slightly different experience—a continuous field may be presented. For example, if looking at red blood cells, even though each ball is only contributing one portion of that field, it appears to be like a continuous field. The images provided by the matrix merge as one and appear as a landscape rather than individual images. In various embodiments, if a user changes an illumination angle, and turns it bright or dark, the microscope may provide the user with 3D information about the sample by producing contrast over the sample based on variations in the sample's 3D profile. Because the illumination stage can move, a user can take the same object and achieve a 3D imaging effect.

Figure 20A:
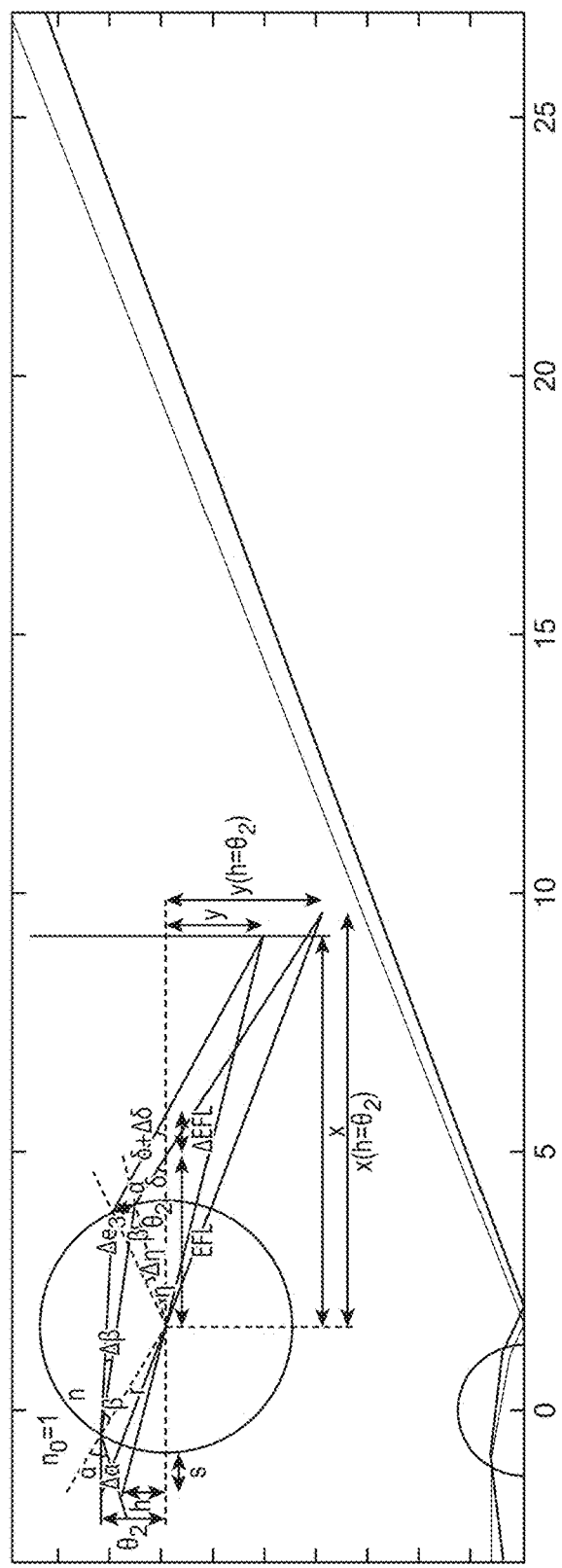
FIG. 20A illustrates a schematic for utilizing a refraction ball lens for projection microscopy with ray-tracing for half of a lens.
Figure 20B:
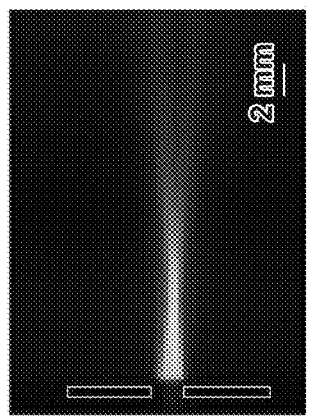
FIG. 20B illustrates a projection illuminated through water containing Fluorescene.

Another feature of the optical microscope 100 is a projection mechanism. FIG. 20A illustrates a schematic of utilizing a refraction ball lens for projection microscopy with ray-tracing for half of a lens. FIG. 20B illustrates a projection illuminated through water containing fluorescein.

The projection mechanism can project images onto a wall, screen, or other surface. The mechanism is a brighter LED such as a high-intensity LED to make the projection more visible. Rather than looking directly into the optical microscope, a user may flip it over and point to a wall in the dark. Two or more people may be looking at the same image at the same time. For example, in a dark room, a high-intensity LED may allow a projection of an image from across the room, making a 1 mm mosquito proboscis appear over 2 meters tall on the wall. The projection may be onto a camera, a wall, a retina, or other location, and the microscope can be a digital image of the projection—the projection optics are the same. In various embodiments, there is also a CCD version that may be provided with one or more cameras integrated in the present system.

Figure 21A:
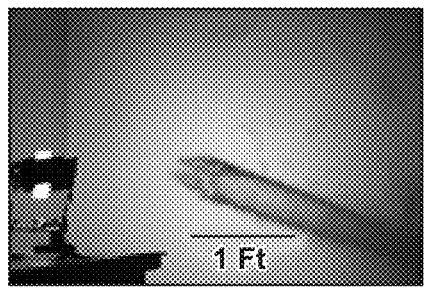
FIG. 21A is a projected image of a mosquito proboscis at an effective magnification of 1500×.
Figure 21B:
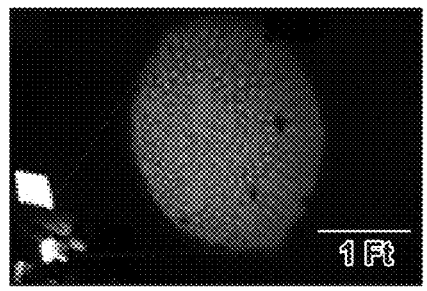
FIG. 21B is a projected image of red blood cells at an effective magnification of 3000×.

The projected mode allows for a number of people to simultaneously view the images. The effective magnification in projection mode is dependent on the distance between the lens and the projected image with the intensity inversely proportional to the distance between the lens and projected image. FIG. 21A is a projected image of a mosquito proboscis at an effective magnification of 1500×. FIG. 21B is a projected image of red blood cells at an effective magnification of 3000×.

Figure 22A:
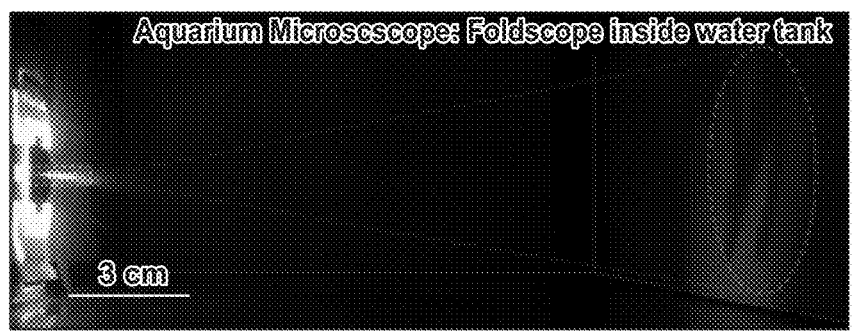
FIG. 22A is a picture of a single ball lens optical microscope submerged under water in accordance with an embodiment.
Figure 22B:
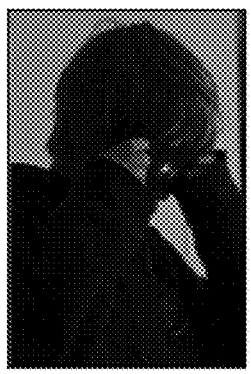
FIG. 22B is a picture of a single ball lens optical microscope projecting an image on the retina of a user in accordance with an embodiment.
Figure 22C:
FIG. 22C is a picture of a single ball lens optical microscope projecting an image on a flat surface in accordance with an embodiment.

FIG. 22B is a picture of a single ball lens optical microscope projecting an image on the retina of a user in accordance with an embodiment.

Optical components of the manufacturing process may include microfluidics, doublets, and other features. Microfluidics may be used to manufacture components. Doublets may be created from liquid and cured lenses and used in combination with a microscope. This may allow for lower costs and timing while increasing magnification. A unique slide position readout may provide a location grid of the sample and allow a user to know where they are on the slide. An integrated cell count mechanism may also be used with the present optical microscope.

Fluidic integration into microscope design may minimize sample handling. An auto-staining process within the microscope involves filters designed from plastic films. The auto-staining process may have the staining dye already integrated.

Several optical microscopes may be contained in a single package. The optical microscopes can be packaged individually similar to a band aid and revealed just before use. This packaging minimizes the risk of having fungus grow on microscope components in humid environments.

The optical microscopes disclosed herein can also be used under water. The microscope can include a water resistant coating such as a polymer coating. Operating under water allows for live imaging of microscopic swimming organisms under water. The under-water image can be projected on the side wall of the aquarium. The thermal gradients generated allow for water to flow past by the sample stage, thus bringing live swimming organisms to be imaged in projection mode through the microscope. FIG. 22A is a picture of a single ball lens optical microscope submerged under water in accordance with an embodiment.

The optical microscopes disclosed herein can be used for disease diagnostics. For example, temperature stable stains are widely available for labeling infectious disease samples including Giemsa and Acridine Orange that are usually used on a standard thin blood smear. Various imaging parameters of optical microscopes disclosed herein, such as field of view, magnification, etc. can be optimized to match the imaging requirements for a disease of interest. The optical microscopes disclosed herein can be configured and built to match a specific disease of interest. In some embodiments disease specific optical microscopes are used instead of general-purpose optical microscopes. For example, various optical microscope configurations were setup and utilized to image freshly prepared diagnostics samples of various parasitic diseases, including *Plasmodium falciparum* (FIG. 23A), *Trypanosom cruzi* (FIG. 23B), *Giradia lamblia* (FIG. 23C), sickle cell disease (FIG. 23D), gram positive and gram negative bacteria (FIG. 23E), *Leishmania donovani* (FIG. 23F) and *Dirofilaria immitis* (FIG. 23G) imaged via various magnification settings. It is noted that the above data (maximum magnification 2500×) was obtained without the use of oil immersion technique or coverslips, which further complicates sample preparation and microscope maintenance in conventional diagnostics assays. This broad dataset reveals the versatility of utility of the optical microscopes disclosed herein in disease diagnostics.

Figure 24A:
FIG. 24A is an image produced by a single ball lens optical microscope in accordance with an embodiment of human chromosomes.
Figure 24B:
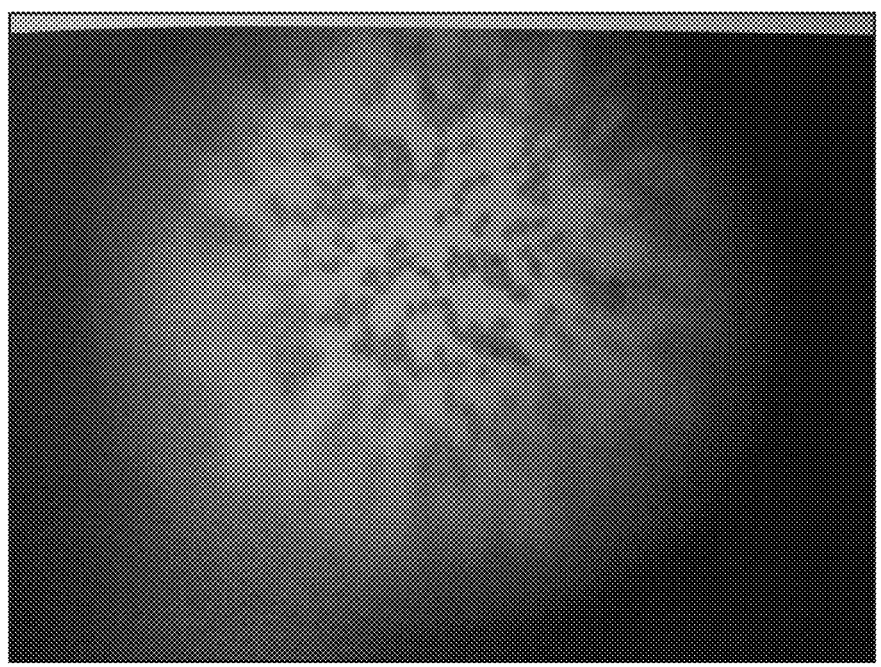
FIG. 24B is an image produced by a single ball lens optical microscope in accordance with an embodiment of a DNA/RNA stain.
Figure 24C:
FIG. 24C is an image produced by a single ball lens optical microscope in accordance with an embodiment of a spinal cord.
Figure 24D:
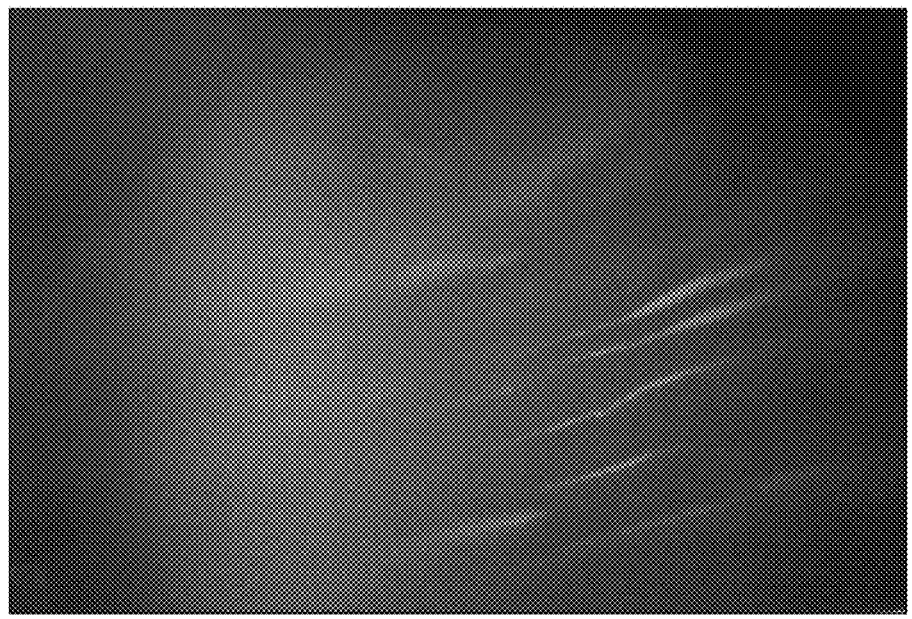
FIG. 24D is an image produced by a single ball lens optical microscope in accordance with an embodiment of skeletal muscle.

FIG. 24A is an image produced by a single ball lens optical microscope in accordance with an embodiment of human chromosomes. FIG. 24B is an image produced by a single ball lens optical microscope in accordance with an embodiment of a DNA/RNA stain. FIG. 24C is an image produced by a single ball lens optical microscope in accordance with an embodiment of a spinal cord. FIG. 24D is an image produced by a single ball lens optical microscope in accordance with an embodiment of skeletal muscle.

Microscopy based diagnostics can be further improved via integrated multiple imaging modalities (such as bright field and fluorescence imaging) to improve sensitivity or increase the total field of view via implementation of parallel array microscopes. The optical microscopes disclosed herein can be packed in a close form to implement Simultaneous Multi-modal Microscopy (SMM) using the miniature optical components and independent optical paths disclosed herein. FIG. 23H is a schematic illustration of a 3×3 lens array with different modalities embedded in an optical microscope in accordance with an embodiment. The use of SMM is largely possible due to the large surface area of the retina (FIG. 23H) that allows for many fields of view to be packed in a closed packed configuration, such as 1+1, 2×2 or 3×3 array microscopes (FIG. 23I) with nine fields of view visible simultaneously (FIG. 23J). Since the optical path for each field of view is independent, different modes of microscopy can be combined to build simultaneous bright and polarization setup (FIG. 23K) or fluorescence from two different wavelengths (FIG. 23L). Simultaneous Multi-modal Microscopy (SMM) enables imaging of samples in multiple modalities simultaneously, which is not possible in conventional optical setups.

FIG. 8B is a schematic illustration of an optical path for an optical microscope in accordance with an embodiment. FIG. 8B illustrates two ball lenses 160. One ball lens 160 directly observes the sample 154 using the light source 142. The eye can directly observe the sample 154 through the optical path 201 and ball lens 160. Simultaneously, the eye can observe the sample through an alternate optical path 203 involving the second ball lens 160 and a mirror 205 that can be tilted to focus on the back of the sample. The mirror can be adjusted to observe a desired area of the sample 154. In some embodiments multiple lenses can be aligned with one or more mirrors to alternately view the sample.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. The present invention descriptions are intended to cover such alternatives, modifications, and equivalents as may be included within the spirit and scope of the invention as defined by the appended claims and otherwise appreciated by one of ordinary skill in the art.

What is claimed is:

1. An optical microscope, comprising:
a first stage having a first end, a second end, a first edge extending from the first end to the second end and a second edge extending from the first end to the second end, a specimen illumination window between the first end and the second end, a first optics stage slot on the first stage between the specimen illumination window and the first end and a second optics stage slot on the first stage between the specimen illumination window and the second end, a first illumination stage slot and a second illumination stage slot on the first stage between the specimen illumination window and the first edge, a third illumination stage slot and a fourth illumination stage slot on the first stage between the specimen illumination window and the second edge with the first stage adapted for supporting a sample directly adjacent to the specimen illumination window located between the first end and the second end;
a second stage engaged with the first stage at a first portion of the second stage in the first optics stage slot and at a second portion of the second stage in the second optics stage slot whereby the second stage is movable relative to the first stage, the second stage including an optic, the optic having a distance of less than about 3 mm from the sample to the opposite side of the optic; and
an illumination stage comprising a light source and a first tab, a second tab, a third tab and a fourth tab, the illumination stage engaged with the first stage with the first tab in the first illumination stage slot, the second tab in the second illumination stage slot, the third tab in the third illumination stage slot and the fourth tab in the fourth illumination stage slot, the illumination stage movable with the second stage, the light source positioned adjacent to the specimen illumination window of the first stage to facilitate viewing the sample using the optic.

2. The optical microscope of claim 1, wherein the second stage is movable laterally relative to the first optics stage slot and the second optics stage slot such that the optic can be positioned over a desired location on the sample.

3. The optical microscope of claim 2, wherein the first stage for supporting the sample comprises a diagnostic coating for providing a visual indication to a user through the optical microscope of a presence of a diagnostic target, wherein the visual indication is viewed using the optic and the diagnostic target is a disease, parasite, or bacteria, or disorder detectable in a bodily fluid.

4. The optical microscope of claim 3, wherein the microscope has a magnification of greater than about 300×.

5. The optical microscope of claim 2, wherein the optical microscope has a resolution of about 1.0 micron or less.

6. The optical microscope of claim 1, wherein the first stage is configured to receive a substrate containing the sample.

7. The optical microscope of claim 6, wherein the first stage of the optical microscope includes a folded portion of the first stage along the first edge adjacent to a slide slot in the first stage to engage along the second edge.

8. The optical microscope of claim 1, wherein the sample is supported directly on the first stage adjacent to the specimen illumination window.

9. The optical microscope of claim 1, the first stage further comprising: a sample area comprising a reagent to react with the sample.

10. The optical microscope of claim 1, wherein when the light source is on one side of the first stage and the optic is spaced apart from the opposite side of the first stage a distance between the light source and the side of the optic farthest from the first stage is from about 1 mm to about 20 mm.

11. The optical microscope of claim 1, wherein the light source includes a light-emitting diode (LED) and the LED has a luminous emittance of 1-100 kLux or more suitable to project an image of the sample.

12. The optical microscope of claim 1, wherein the light source includes a light-emitting diode (LED) and the LED has a power of 10-1,000 Lux suitable to illuminate the sample so that a user's eye may perceive the image of the sample.

13. The optical microscope of claim 1, wherein the optic includes a substantially spherical lens having a diameter, wherein the illumination stage includes an aperture having a diameter of about ¼ to about ⅔ of the diameter of the substantially spherical lens.

14. The optical microscope of claim 1, wherein the illumination stage is coupled to the second stage by engaging a first contact pad tab and a second contact pad tab of the illumination stage with a first contact pad slot and a second contact pad slot of the second stage.

15. The optical microscope of claim 14, wherein the light source is on while pressing the first contact pad tab and the second contact pad tab against the second stage.

16. The optical microscope of claim 1, wherein in use the optical microscope having an optical alignment of the illumination stage, first stage, and second stage achieved by flexing the second stage.

17. The optical microscope of claim 16, wherein the optical alignment has an accuracy of about 10 microns or less.

18. The optical microscope of claim 1, wherein the first stage, the second stage and the illumination stage comprises one or more of paper, polymer, and metal.

19. The optical microscope of claim 1, further comprising: a power source engaged with the illumination stage and configured to provide power to the light source.

20. The optical microscope of claim 1, wherein the optical microscope is a bright field microscope.

21. The optical microscope of claim 1, further comprising a light filter, wherein the optical microscope is a fluorescence microscope.

22. The optical microscope of claim 1, wherein the optic comprises a substantially spherical lens with a diameter of about 200 μm to about 1,000 μm and the second stage including an opening with the lens in the opening.

23. The optical microscope of claim 1 the first stage further comprising a sleeve slide extending from the first edge, the slide sleeve having a slide slot, a slide tab and a slide viewing window between the slide slot and the slide tab.

24. The optical microscope of claim 23 wherein in use the slide sleeve is folded over the first stage to engage the slide tab adjacent to the second edge with the slide viewing window in proximity to the specimen illumination window.

* * * * *